United States Patent [19]
Barbachyn et al.

[11] Patent Number: 6,069,141
[45] Date of Patent: May 30, 2000

[54] SUBSTITUTED AMINOPHENYL ISOXAZOLINE DERIVATIVES USEFUL AS ANTIMICROBIALS

[75] Inventors: Michael Robert Barbachyn; Joel Morris; Donn G. Wishka; Gary J. Cleek; Richard Charles Thomas, all of Kalamazoo, Mich.

[73] Assignee: Pharmacia & Upjohn Company, Kalamazoo, Mich.

[21] Appl. No.: 09/243,871

[22] Filed: Feb. 3, 1999

Related U.S. Application Data

[60] Provisional application No. 60/075,126, Feb. 13, 1998.
[51] Int. Cl.$^7$ .................. A61K 31/422; A61K 31/5377; A61N 31/04; C07D 413/10
[52] U.S. Cl. ...................... 514/236.8; 514/378; 544/58.2; 544/58.6; 544/137; 544/367; 548/240; 548/255
[58] Field of Search .............................. 548/240; 544/137, 544/367; 514/236.8

[56] References Cited

U.S. PATENT DOCUMENTS

| | | |
|---|---|---|
| 3,769,295 | 10/1973 | Hoyle et al. . |
| 4,283,403 | 8/1981 | Davenport . |
| 5,547,950 | 8/1996 | Hutchinson et al. . |
| 5,990,136 | 11/1999 | Barbachyn et al. ..................... 548/240 |

FOREIGN PATENT DOCUMENTS

| | | |
|---|---|---|
| 0 352 781 | 1/1990 | European Pat. Off. . |
| 2725763 | 12/1977 | Germany . |
| WO95/07271 | 3/1995 | WIPO . |
| WO95/14680 | 6/1995 | WIPO . |
| WO95/14684 | 6/1995 | WIPO . |
| WO95/25106 | 9/1995 | WIPO . |
| WO96/13502 | 5/1996 | WIPO . |
| WO96/23788 | 8/1996 | WIPO . |
| WO97/21708 | 6/1997 | WIPO . |
| WO98 07708 | 2/1998 | WIPO . |

OTHER PUBLICATIONS

SS Ghabrial, et al., Acta Chemica Scand. B41, pp. 426–434 (1987).

*Primary Examiner*—Robert W. Ramsuer
*Attorney, Agent, or Firm*—Lucy X. Yang

[57] ABSTRACT

The present invention provides novel substituted amionphenyl isoxazoline derivatives of formula I

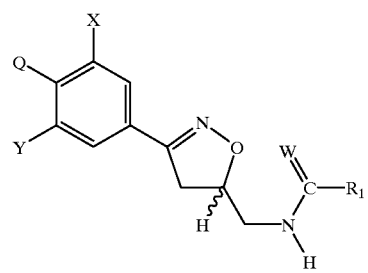

wherein $R_1$ is H, alkyl, cycloalkyl, alkoxy, amino, or alkylamino;

X and Y are the same and different and are H, F, or $CH_3$; W is O, or S;

Q is a 4-, 5-, 6-, 7-, or 9-membered heterocyclic moiety containing one or more nitrogen, sulfur and/or oxygen. The compounds of the invention are useful as antimicrobial agents for preventing and treating infectious diseases.

18 Claims, No Drawings

SUBSTITUTED AMINOPHENYL ISOXAZOLINE DERIVATIVES USEFUL AS ANTIMICROBIALS

CROSS-REFERENCE TO RELATED APPLICATIONS

This application claims the benefit of provisional application U.S. Ser. No. 60/075,126, filed Feb. 13, 1998, under 35 USC$_{119}$(e)(i).

FIELD OF THE INVENTION

The present invention relates to novel substituted aminophenyl isoxazoline derivatives, to pharmaceutical compositions containing them as active ingredients, and to methods of using them. The compounds of the invention are useful as antimicrobial agents for preventing and treating infectious diseases.

BACKGROUND OF THE INVENTION

Antibacterial agents such as oxazolidinones are a class of known orally-active, synthetic antibacterial agents and there are numerous references in the art disclosing a variety of oxazolidinone derivatives. For example, U.S. Pat. Nos. 4,705,799 and 5,523,403 and European Patent Application 0,316,594 disclose :substituted phenyl-2-oxazolidinones, including the sulfides, sulfoxides, sulfones, sulfonamides, nitriles, acetamides and a tropane ring. U.S. Pat. Nos. 4,948,801; 5,254,577 and 5,130,316 disclose arylbenzene oxazolidinyl compounds, wherein the aryl includes the (un)substituted phenyl and pyridyl groups. European Patent Applications 0,697,412; 0,694,544; 0,694,543 and 0,693,491 disclose 5 to 9-membered heteroaryl-oxazolidinones having one to three atoms selected from the group consisting of sulfur, nitrogen and oxygen.

This invention describes substituted amionphenyl isoxazoline derivatives useful as antibacterial agents. The compounds of the invention are novel and distinct from antibaterial oxazolidinones in that the usual oxazolidinone rings are replaced by an isoxazoline moiety. These compounds have antibacterial activity comparable to the corresponding oxazolidinones. They are effective against a number of human and veterinary pathogens, including gram-positive aerobic bacteria such as multiply-resistant staphylococci and streptococci, as well as anaerobic organisms such as bacteroides and clostridia species, and acid-fast organisms such as *Mycobacterium tuberculosis* and *Mycobacterium avium*.

INFORMATION DISCLOSURE

U.S. Pat. No. 4,283,403 discloses 3-aryl-2-isoxazolines useful for the protection of plants from diseases.

Danish Patent No. 2,725,763 discloses substituted 2-isoxazolines which is fungicidal against phytophthora infestation on tomatoes. The compounds also show antibacterial activity.

U.S. Pat. No. 3,769,295 discloses nitrofuryl derivatives of 5-substituted isoxazolines useful as antimicrobial agents.

WO 95/14680 A1 discloses 3-aryl-2-isoxazolines which is useful in inhibiting PDE$_{IV}$, the treatment of inflammatory diseases and the treatment of AIDs, asthma, arthritis, etc.

S. S. Ghabrial, et al., Acta Chemica Scandinavica, B 41, pp. 426–434 (1987) discloses the synthesis of heteroaromatic compounds via the isoxazoline route.

U.S. Pat. No. 5,547,950 discloses oxazolidinones containing a substituted diazine moiety and their use as antimicrobials.

International Publication No. WO 95/07271 discloses substituted oxazine and thiazine oxazolidinone antimicrobials.

International Publication No. WO 9514684 discloses esters of substituted-hydroxyacetyl piperazine phenyl oxazolidinones.

International Publication No. WO 95/25106 discloses oxazolidinone derivatives and pharmaceutical compositions containing them.

International Publication No. WO 96/13502 discloses phenyloxazolidinone antimicrobials.

International Publication No. WO 96/23788 discloses hetero-aromatic ring substituted phenyloxazolidinone antimicrobials.

International Publication No. WO 97/21708 discloses 4-pyrimidinyl- or 4-pyrazinyl-piperazinyl-phenyl-oxazolidinone derivatives.

SUMMARY OF THE INVENTION

The present invention provides a compound of formula I

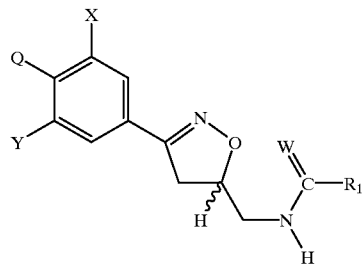

or pharmaceutically acceptable salts thereof wherein:

R$_1$ is
  (a) H,
  (b) C$_{1-8}$ alkyl, which may be substituted with one or more halo, —OH, C$_{1-4}$ alkoxy or C$_{1-4}$ acyloxy,
  (c) C$_{3-6}$ cycloalkyl,
  (d) C$_{1-8}$ alkoxy,
  (e) amino, or
  (f) NH(C$_{1-3}$ alkyl), wherein C$_{1-3}$ alkyl may be substituted with one or more halo;

X and Y are independently H, F, or CH$_3$;

W is O, or S;

Q is
  (a) a 5-membered heterocyclic moiety having one to four nitrogen atoms selected from structures consisting of i, ii, iii, iv, v, vi, vii, viii, and ix;

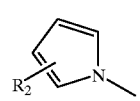

i

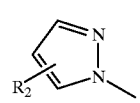

ii iii
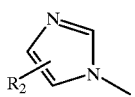
iv
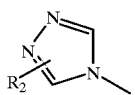
v
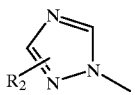
vi
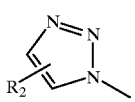
vii
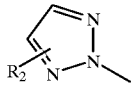
viii
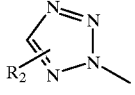
ix
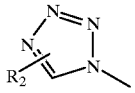
(b) a 9-membered heterocyclic moiety having one to four nitrogen atoms selected from structures consisting of x, xi, xii, xiii, xiv, xv, xvi, xvii, and xviii;
x
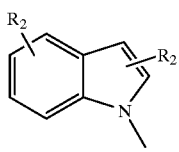
xi
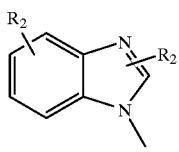
xii
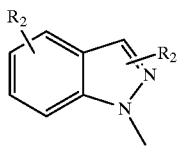
xiii
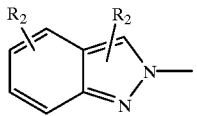
xiv
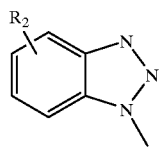
xv
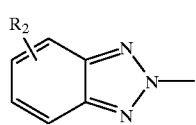
xvi
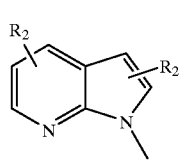
xvii
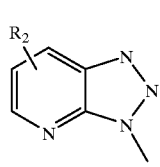
xviii
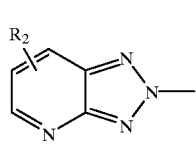
(c) a heterocyclic ring having a nitrogen atom selected from structures consisting of xix, xx, xxi, xxii, and xxiii;
xix
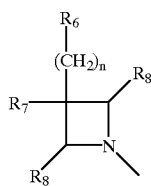
xx
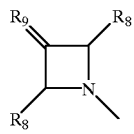
xxi
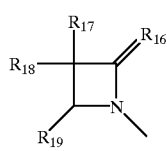

-continued

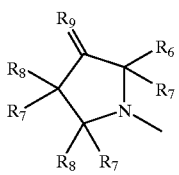

(d)

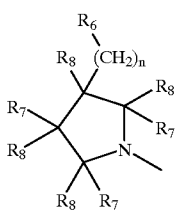

(e)

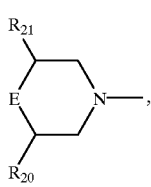

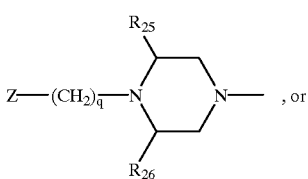, or (f)

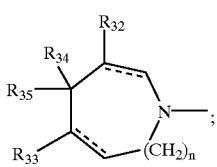

wherein $R_2$ is
- (a) H,
- (b) halo,
- (c) —OH,
- (d) —OR$_3$,
- (e) —SR$_3$,
- (f) —S(O)$_t$R$_3$,
- (g) —CN,
- (h) —O$_2$CR$_3$,
- (i) —NHC(=O)R$_3$,
- (j) —NHCO$_2$R$_3$,
- (k) —NHSO$_2$R$_3$,
- (l) —CO$_2$R$_4$,
- (m) —C(=O)N(R$_3$)$_2$,
- (n) —C(=O)R$_3$,
- (o) C$_{1-8}$ alkyl,
- (p) C$_{3-8}$ cycloalkyl, wherein groups (o) and (p) may be substituted with one or more of the preceding groups (a)–(n),
- (q) phenyl, which may be substituted with one or more of the preceding groups (a)–(p),
- (r) —CH=CHCO$_2$Et, or
- (s) —C(=NR$_4$)R$_5$;

$R_3$ is
- (a) H,
- (b) C$_{1-6}$ alkyl,
- (c) C$_{3-8}$ cycloalkyl, wherein groups (b) and (c) may be substituted with one or more of halo, —OH, C$_{1-4}$ alkoxy, C$_{1-4}$ acyl, C$_{1-4}$ acyloxy, or —OC(=O)CH$_2$N(CH$_3$)$_2$, or
- (d) phenyl, which may be substituted with one or more of the preceding groups (b) to (c);

$R_4$ is —OH or —OCH$_3$;

$R_5$ is H, or —CH$_3$;

$R_6$ is
- (a) H,
- (b) —OR$_{10}$,
- (c) —SR$_{10}$,
- (d) —NR$_{11}$R$_{12}$,
- (e) —CN,
- (f) C$_{1-4}$ alkoxycarbonyl,
- (g) carboxamide,
- (h) C$_{1-4}$ acyl, which may be substituted with one or more halo, —OH, C$_{1-4}$ alkoxy or C$_{1-4}$ acyloxy,
- (i) —N(OH)(C$_{1-6}$ alkyl),
- (j) —N(OH)CH$_2$ phenyl,
- (k) —NSO$_2$(C$_{1-6}$ alkyl) wherein C$_{1-6}$ alkyl may be substituted with one or more halo, C$_{1-6}$ alkoxy or phenyl, or
- (l) F;

$R_7$ is
- (a) H,
- (b) —OH,
- (c) —O(C$_{1-6}$ alkyl),
- (d) C$_{1-4}$ alkyl,
- (e) phenyl, or
- (f) F;

$R_8$ is
- (a) H,
- (b) C$_{1-3}$ alkyl, which may be substituted with halo, —OH, —CO$_2$ C$_{1-4}$ alkyl, C$_{1-3}$ acyloxy, C$_{1-3}$ alkyoxy or —N(C$_{1-4}$ alkyl)$_2$,
- (c) phenyl, or
- (d) pyridyl;

$R_9$ is O, S, —NR$_{13}$, or —CR$_{14}$R$_{15}$;

$R_{10}$ is
- (a) H,
- (b) C$_{1-8}$ alkyl, which may be substituted with one or more halo, —CN, —OH, C$_{1-8}$ alkoxy, C$_{1-8}$ acyloxy, C$_{1-4}$ alkoxycarbonyl, or phenyl,
- (c) C$_{1-8}$ acyl, which may be substituted with one or more —OH, C$_{1-8}$ alkoxy, C$_{1-8}$ acyloxy,
- (d) C$_{1-8}$ alkoxycarbonyl,
- (e) carboxamide, which may be substituted with a C$_{1-4}$ alkyl or phenyl on the carboxamide nitrogen, or
- (f) phenyl, which may be substituted with one or more halo, —CN, C$_{1-3}$ alkoxy, C$_{1-3}$ alkoxycarbonyl or C$_{1-4}$ alkyl;

$R_{11}$ and $R_{12}$ are the same and different and are
- (a) H,
- (b) C$_{1-8}$ alkyl, which may be substituted with one or more halo, —CN, —OH, C$_{1-8}$ alkoxy, C$_{1-8}$ acyloxy, C$_{1-8}$ alkoxycarbonyl, phenyl,
- (c) C$_{1-8}$ acyl, which may be substituted with one or more —OH, amino, C$_{1-8}$ alkoxy, C$_{1-8}$ acyloxy, C$_{1-4}$ acylamino, (d) benzoyl, which may be substituted with one or more halo, —OH, amino, $C_{1-8}$ alkoxy, $C_{1-8}$ acyloxy, $C_{1-4}$ acylamino, $C_{1-4}$ alkoxycarbonylamino,
(e) $C_{1-8}$ alkoxycarbonyl,
(f) benzyloxycarbonyl,
(g) tertbutoxycarbonyl,
(h) carboxamide, which may be substituted with a $C_{1-4}$ alkyl or phenyl on the carboxamide nitrogen,
(i) trifluoracetyl, or
(j) $C_{1-6}$ acyl;

$R_{13}$ is H, —$OR_{10}$, —$NHR_{10}$, or $C_{1-8}$ alkyl, which may be substituted with phenyl;

$R_{14}$ and $R_{15}$ are independently
(a) H,
(b) $C_{1-4}$ alkyl, which may be substituted with halo, —OH, $C_{1-4}$ alkoxy, $C_{1-4}$ alkoxycarbonyl, or phenyl,
(c) $C_{1-8}$ acyl,
(d) $C_{1-4}$ alkoxycarbonyl,
(e) —CN, or
(f) F;

$R_{16}$ is O, or S;

$R_{17}$ and $R_{18}$ are independently
(a) H,
(b) $C_{1-4}$ alkyl, which may be substituted with halo, —OH or $C_{1-4}$ alkoxy,
(c) —OH,
(d) $C_{1-4}$ alkoxy, which may be substituted with —OH or $C_{1-4}$ alkoxy,
(e) $NR_{11}R_{12}$, or
(f) $C_{1-4}$ acyloxy;

$R_{19}$ is H, or —$CH_3$;

E is
(a) —O—, or
(b) —S(=O)$_m$—;

$R_{20}$ is
(a) H,
(b) —$CH_3$,
(c) —CN,
(d) —$CO_2H$,
(e) —$CO_2R_{22}$, or
(f) —$(CH_2)_iR_{23}$;

$R_{21}$ is H, or —$CH_3$;

$R_{22}$ is
(a) H,
(b) $C_{1-6}$ alkyl, which may be substituted with halo, —OH, $C_{1-4}$ alkoxy, $C_{1-4}$ acyloxy or —O—$CH_2$-phenyl,
(c) $C_{3-6}$ cycloalkyl,
(d) amino,
(e) —N($C_{1-6}$ alkyl)$_2$,
(f) —NH($C_{1-6}$ alkyl), or
(g) $C_{1-6}$ alkoxy;

$R_{23}$ is
(a) —OH,
(b) —$OR_{22}$,
(c) —OC(=O)$R_{22}$,
(d) amino,
(e) —NHC(=O)$R_{22}$, or
(f) —N($R_{24}$)$_2$;

$R_{24}$ is
(a) H,
(b) $C_{1-4}$ alkyl, which may be substituted with halo, —OH, $C_{1-4}$ alkoxy, amino, —N($C_{1-6}$ alkyl)$_2$, or —NH($C_{1-6}$ alkyl), or (c) p-toluenesulfonyl;

wherein Z is
(a) H,
(b) —C(=O)$R_{27}$,
(c) $C_{1-6}$ alkyl,
(d) benzyl,
(e) phenyl, wherein groups (d) and (e) may be substituted with one or more halo, —$OCH_3$, —OH, amino or $C_{1-4}$ alkyl,
(f) —$OR_{28}$,
(g) —OC(=O)$R_{29}$,
(h) —S—$C_{1-6}$ alkyl,
(i) —$SO_2$—$C_{1-6}$ alkyl,
(j) phenylsulfonyl,
(k) p-toluenesulfonyl,
(l) —$SO_2$—N($R_{30}$)$_2$,
(m) —C(O)—$OR_{31}$,
(n) —C(O)—N($R_{30}$)$_2$,
(o) —N($R_{30}$)$_2$, or
(p) a 6-membered heterocyclic moiety having one to three nitrogen atoms selected from structures consisting of xxiv, xxv, xxvi, xxvii, xxviii, xxix,

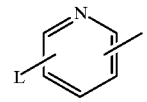

xxiv

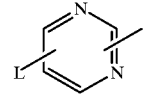

xxv

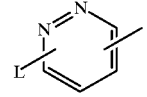

xxvi

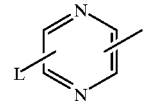

xxvii

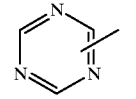

xxviii

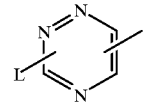

xxix

L is
(a) H, amino, $C_{1-4}$, alkyl, or halo;

$R_{25}$ and $R_{26}$ are independently
(a) H,
(b) $C_{1-6}$ alkyl, or
(c) $C_{3-6}$ cycloalkyl;

$R_{27}$ is
(a) $C_{1-6}$ alkyl,
(b) $C_{1-8}$ alkylhydroxyl, (c) phenyl, or
(d)

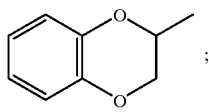

$R_{28}$ is
(a) H,
(b) $C_{1-6}$ alkyl,
(c) vinyl, or
(d) phenyl, which may be substituted with one to more halo, $C_{1-4}$ alkoxy, —OH, amino or $C_{1-4}$ alkyl;
$R_{29}$ is $C_{1-6}$ alkyl, or phenyl;
$R_{30}$ is independently
(a) H,
(b) $C_{1-4}$ alkyl, or
(c) phenyl, which may be substituted with $C_{1-4}$ alkyl or $C_{1-4}$ alkoxy;
$R_{31}$ is
(a) $C_{1-6}$ alkyl,
(b) phenyl, which may be substituted with $C_{1-4}$ alkyl or $C_{1-4}$ alkoxy, or
(c) benzyl, which may be substituted with $C_{1-4}$ alkyl or $C_{1-4}$ alkoxy;
wherein $R_{32}$ and $R_{33}$ are independently
(a) H,
(b) halo,
(c) $C_{1-8}$ alkyl, which may be substituted with one or more $R_{45}$,
(d) $C_{3-6}$ cycloalkyl,
(e) —$(CH_2)_m$—$OR_{36}$, or
(f) —C(=O)—$R_{38}$;
$R_{34}$ and $R_3$, are independently
(a) H,
(b) $C_{1-8}$ alkyl, which may be substituted with one or more $R_{45}$,
(c) $C_{1-8}$ alkoxy,
(d) $C_{1-8}$ alkylthio,
(e) —$(CH_2)_m$—$OR_{39}$,
(f) —O—$(CH_2)_m$—$OR_{39}$,
(g) —$NR_{40}R_{41}$,
(h) —N=CH—$NR_{42}R_{43}$,
(i) —C(=O)—$NR_{40}R_{41}$, or
(j) —$(CH_2)_m$—C(=A)—$R_{38}$, wherein A is O or ethyleneketal,
or $R_{34}$ and $R_{35}$ together to form
(k) =O,
(l) =$NR_{44}$,
(m) =S, or
(n) =$CR_{42}R_{43}$;
$R_{36}$ and $R_{37}$ are independently
(a) H,
(b) $C_{1-8}$ alkyl, which may be substituted with one or more $R_{45}$, or
(c) —$CH_2OCH_3$;
$R_{38}$ is
(a) H,
(b) —$(CH_2)_m$—OH,
(c) $C_{1-8}$ alkyl, which may be substituted with one or more $R_{45}$,
(d) $C_{1-8}$ alkoxy,
(e) —O—$CH_2$—O—C(=O)—$R_{36}$, or
(f) —$(CH_2)_m$—C(=O)—$OR_{36}$;
$R_{39}$ is
(a) H,
(b) $C_{1-8}$ alkyl, which may be substituted with one or more $R_{45}$,
(c) $C_{2-8}$ alkenyl,
(d) —$(CH_2)_m$—$OR_{36}$,
(e) —$(CH_2)_m$—C(=O)—$R_{38}$,
(f) —C(=O)—$(CH_2)_m$—$OR_{43}$, or
(g) tosyl;
$R_{40}$ and $R_{41}$ are independently
(a) H,
(b) —$(CH_2)_m$—$OR_{36}$,
(c) $C_{1-8}$ alkyl, which may be substituted with one or more $R_{45}$,
(d) —C(=O)—$R_{38}$,
(e) —C(=O)—$NR_{36}R_{37}$,
(f) —$(CH_2)p$-phenyl,
(g) thiazol-2-yl,
or $R_{40}$ and $R_{41}$ together to form
(h) pyrrolidino,
(i) piperidino,
(j) piperazino,
(k) morpholino, or
(l) thiomorpholino,
wherein groups (h) to (l) may be substituted with $C_{1-8}$ alkyl or —$(CH_2)_m$—OH;
$R_{42}$ and $R_{43}$ are independently
(a) H,
(b) $C_{1-8}$ alkyl, which may be substituted with one or more $R_{45}$,
(c) —C(=O)—$R_{38}$, or
(d) —$(CH_2)p$-phenyl;
$R_{44}$ is
(a) H,
(b) —$OR_{39}$,
(c) $C_{1-8}$ alkyl, which may be substituted with one or more $R_{45}$,
(d) $C_{1-8}$ alkoxy,
(e) —$(CH_2)p$-phenyl,
(f) —$NR_{40}R_{41}$,
(g) —NH—C(=NH)—$NH_2$,
(h) [1,2,4]triazol-4-yl, or
(i) —CN;
$R_{45}$ is
(a) halo,
(b) —OH,
(c) —CN,
(d) $C_{1-6}$ alkoxy,
(e) amino,
(f) —$N(C_{1-6}$ alkyl$)_2$,
(g) —$NH(C_{1-6}$ alkyl), or
(h) carboxyl;
═ is a double bond or a single bond;
i is 1 or 2; m is 0, 1 or 2; n is 0 or 1; p is 1, 2, 3 or 4; and q is 0, 1, 2, 3 or 4.

These compounds have antimicrobial activity against a number of human and veterinary pathogens, including gram-positive aerobic bacteria such as multiply-resistant staphylococci and streptococci, as well as anaerobic organisms such as bacteroides and clostridia species, and acid-fast organisms such as *Mycobacterium tuberculosis* and *Mycobacterium avium*.

DETAILED DESCRIPTION OF THE INVENTION

For the purpose of the present invention, the carbon content of various hydrocarbon containing moieties is indicated by a prefix designating the minimum and maximum number of carbon atoms in the moiety, i.e., the prefix Cij defines the number of carbon atoms present from the integer "i" to the integer "j", inclusive. Thus, $C_{1-4}$ alkyl refers to alkyl of 1–4 carbon atoms, inclusive, or methyl, ethyl, propyl, butyl and isomeric forms thereof.

The terms "$C_{1-3}$ alkyl", "$C_{1-4}$ alkyl", "$C_{1-6}$ alkyl", and "$C_{1-8}$ alkyl" refer to an alkyl group having one to three, one to four, one to six, or one to eight carbon atoms respectively such as, for example, methyl, ethyl, propyl, butyl, pentyl, hexyl, heptyl, octyl and their isomeric forms thereof.

The term "$C_{2-8}$ alkenyl" refers to at least one double bond alkenyl group having two eight carbon atoms such as, for example, ethenyl, propenyl, butenyl, pentenyl, pentdienyl, hexenyl, hexdienyl, heptenyl, heptdienyl, octenyl, octdienyl, octatrienyl, and their isomeric forms thereof.

The terms "$C_{3-6}$ cycloalkyl", and "$C_{3-8}$ cycloalkyl" refer to a cycloalkyl having three to six, or three to eight carbon atoms respectively such as, for example, cyclopropyl, cyclobutyl, cyclopentyl, cyclohexyl, cycloheptyl, cyclooctyl, and their isomeric forms thereof.

The terms "$C_{1-3}$ alkoxy", "$C_{1-4}$ alkoxy", "$C_{1-6}$ alkoxy", and "$C_{1-8}$ alkoxy" refer to an alkyl group having one to three, one to four, one to six, or one to eight carbon atoms respectively attached to an oxygen atom such as, for example, methoxy, ethoxy, propyloxy, butyloxy, pentyloxy, hexyloxy, heptyloxy, or octyloxy and their isomeric forms thereof.

The terms "$C_{1-4}$ acyl", "$C_{1-6}$ acyl", and "$C_{1-8}$ acyl" refer to a —C(=O)R group, wherein R is an alkyl group of one to four, one to six or one to eight carbon atoms and their isomeric forms thereof.

The terms "$C_{1-3}$ alkoxycarbonyl", "$C_{1-6}$ alkoxycarbonyl", and "$C_{1-8}$ alkoxycarbonyl" refer to a —CO$_2$R group, wherein R' is an alkyl group of one to three, one to six, or one to eight carbon atoms and their isomeric forms thereof.

The terms "$C_{1-3}$ acyloxy", "$C_{1-4}$ acyloxy", and "$C_{1-8}$ acyloxy" refer to a —OC(=O)R group, wherein R" is an alkyl group of one to three, one to four, or one to eight carbon atoms and their isomeric forms thereof.

The term "$C_{1-4}$ acylamino" refers to a —NHC(=O)R group, wherein R is an alkyl group of one to four carbon atoms and their isomeric forms thereof.

The term "$C_{1-4}$ alkoxycarbonylamino" refers to —NHC(=O)OR, wherein R is an alkyl group of one to four carbon atoms and their isomeric forms thereof.

The term "$C_{1-8}$ hydroxyl" refers to an alkyl group having one to eight carbon atoms and isomeric forms thereof attached to a hydroxy group.

The term "$C_{1-8}$ alkylthio" refers to an alkyl group having one to six carbon atoms and isomeric forms thereof attached to a sulfur atom.

The term "halo" refers to fluoro, chloro, bromo, or iodo.

The compounds of the present invention can be converted to their salts, where appropriate, according to conventional methods.

The term "pharmaceutically acceptable salts" refers to acid addition salts useful for administering the compounds of this invention and include hydrochloride, hydrobromide, hydroiodide, sulfate, phosphate, acetate, propionate, lactate, mesylate, maleate, malate, succinate, tartrate, citric acid, 2-hydroxyethyl sulfonate, fumarate and the like. These salts may be in hydrated form.

The compounds of formula I of this invention contain a chiral center at C5 of the isoxazoline ring, and as such there exist two enantiomers or a racemic mixture of both. This invention relates to both the enantiomers, as well as mixtures containing both the isomers. The preferred enantiomer is the one having (R)—absolute configuration at C-5 of the isoxazoline ring. In addition, depending on the substituents, additional chiral centers and other isomeric forms may be present in any of the Q or $R_1$ group, and this invention embraces all possible stereoisomers and geometric forms in these groups.

The compounds below are typical phenyl isoxazolines of this invention. It will be understood that the named compounds do not limit the scope of the invention, but are named merely to help one skilled in the art to understand the invention.

1. (±)-N-[[4,5-Dihydro-3-[4-(1H-imidazol-1-yl)phenyl]-5-isoxazolyl]methyl]acetamide,
2. (±)-N-[[4,5-Dihydro-3-[4-[4-(hydroxyacetyl)-1-piperazinyl]phenyl]-5-isoxazolyl]methyl]acetamide,
3. (±)-N-[[3-[3-Fluoro-4-(1-piperazinyl)phenyl]-4,5-dihydro-5-isoxazolyl]methyl]acetamide,
4. (±)-N-[[3-[3-Fluoro-4-[4-(hydroxyacetyl)-1-piperazinyl]phenyl]-4,5-dihydro-5-isoxazolyl]methyl]acetamide,
5. (±)-N-[[3-[3-Fluoro-4-(1-pyrrolidinyl)phenyl]-4,5-dihydro-5-isoxazolyl]methyl]acetamide,
6. (±)-N-[[3-[3-Fluoro-4-(1H-imidazol-1-yl)phenyl]-4,5-dihydro-5-isoxazolyl]methyl]acetamide,
7. (±)-N-[[3-[4-(4-Cyano-1H-pyrazol-1-yl)-3-fluorophenyl]-4,5-dihydro-5-isoxazolyl]methyl]acetamide,
8. (±)-N-[[3-[4-(4-Cyano-1H-1,2,3-triazol-1-yl)-3-fluorophenyl]-4,5-dihydro-5-isoxazolyl]methyl]acetamide,
9. (±)-N-[[3-[3,5-Difluoro-4-(1-piperazinyl)phenyl]-4,5-dihydro-5-isoxazolyl]methyl]acetamide,
10. (±)-N-[[3-[3,5-Difluoro-4-(4-morpholinyl)phenyl]-4,5-dihydro-5-isoxazolyl]methyl]acetamide,
11. (−)-N-[[3-[3-Fluoro-4-(1-pyrrolidinyl)phenyl]-4,5-dihydro-5-isoxazolyl]methyl]acetamide,
12. (−)-N-[[3-[3-Fluoro-4-(1H-pyrrol-1-yl)phenyl]-4,5-dihydro-5-isoxazolyl]methyl]acetamide,
13. (−)-N-[[3-[3-Fluoro-4-(1H-imidazol-1-yl)phenyl]-4,5-dihydro-5-isoxazolyl]methyl]acetamide,
14. (−)-N-[[3-[4-(4-Cyano-1H-pyrazol-1-yl)-3-fluorophenyl]-4,5-dihydro-5 -isoxazolyl]methyl]acetamide,
15. (−)-N-[[3-[3-Fluoro-4-(3-formyl-1H-pyrrol-1-yl)phenyl]-4,5-dihydro-5-isoxazolyl]methyl]acetamide,
16. (−)-N-[[3-[3-Fluoro-4-[3-[(hydroxyimino)methyl]-1H-pyrrol-1-yl]phenyl]-4,5-dihydro-5-isoxazolyl]methyl]acetamide,
17. (−)-N-[[3-[4-(3-Cyano-1H-pyrrol-1-yl)-3-fluorophenyl]-4,5-dihydro-5-isoxazolyl]methyl]acetamide,
18. (−)-N-[[3-[3-Fluoro-4-(1H-pyrrol-1-yl)phenyl]-4,5-dihydro-5-isoxazolyl]methyl]ethanethioamide, 19. (+)-N-[[3-[3-Fluoro-4-(3-formyl-1H-pyrrol-1-yl) phenyl]-4,5-dihydro-5-isoxazolyl]methyl] ethanethioamide,
20. (−)-N-[[3-[3-Fluoro-4-[3-(hydroxymethyl)-1H-pyrrol-1-yl]phenyl]-4,5-dihydro-5-isoxazolyl]methyl]acetamide,
21. (−)-N-[[3-[4-(4-Acetyl-1-piperazinyl)-3-fluorophenyl]-4,5-dihydro-5-isoxazolyl]methyl]acetamide,
22. (−)-N-[[3-[4-[4-[(2,3-Dihydro-1,4-benzodioxin-2-yl)carbonyl]-1-piperazinyl]-3-fluorophenyl]-4,5-dihydro-5-isoxazolyl]methyl]acetamide,
23. (−)-N-[[3-[3-Fluoro-4-[4-(hydroxyacetyl)-1-piperazinyl]phenyl]-4,5-dihydro-5-isoxazolyl]methyl]acetamide,
24. (−)-N-[[3-[3-Fluoro-4-(4-morpholinyl)phenyl]-4,5-dihydro-5-isoxazolyl]methyl]acetamide,
25. (−)-N-[[3-[3,5-Difluoro-4-(1-piperazinyl)phenyl]-4,5-dihydro-5-isoxazolyl]methyl]acetamide,
26. (−)-N-[[3-[4-[4-[(2,3-Dihydro-1,4-benzodioxin-2-yl)carbonyl]-1-piperazinyl]-3,5-difluorophenyl]-4,5-dihydro-5-isoxazolyl]methyl]acetamide,
27. (−)-N-[[3-[3,5-Difluoro-4-[4-(hydroxyacetyl)-1-piperazinyl]phenyl]-4,5-dihydro-5-isoxazolyl]methyl]acetamide,
28. (−)-N-[[3-[3,5-Difluoro-4-(1H-imidazol-1-yl)phenyl]-4,5-dihydro-5-isoxazolyl]methyl]acetamide,
29. N-[[3-[3,5-Difluoro-4-(1H-imidazol-1-yl)phenyl]-4,5-dihydro-5-isoxazolyl]methyl]ethanethioamide,
30. (−)-N-[[3-[3,5-Difluoro-4-(4-morpholinyl)phenyl]-4,5-dihydro-5-isoxazolyl]methyl]ethanethioamide,
31. (−)-N-[[3-[3,5-Difluoro-4-(4-morpholinyl)phenyl]-4,5-dihydro-5-isoxazolyl]methyl]acetamide,
32. N-({3-[3-fluoro-4-(4-thiomorpholinyl)phenyl]-4,5-dihydro-5-isoxazolyl}methyl)acetamide,
33. N-({3-[3-fluoro-4-(1-oxo-1lambda$^4$,4-thiazinan-4-yl) phenyl}-4,5-dihydro-5-isoxazolyl}methyl)acetamide,
34. N-({3-[3-fluoro-4-(4-thiomorpholinyl)phenyl]-4,5-dihydro-5-isoxazolyl}methyl)ethanethioamide, or
35. N-({3-[3-fluoro-4-(1-oxo-1lambda$^4$,4-thiazinan-4-yl) phenyl}-4,5-dihydro-5-isoxazolyl}methyl) ethanethioamide.

The compounds of this invention can be prepared in accordance to one or more of the processes discussed below. In SCHEMES I, II, III, IV and V below, X, Y, Q and $R_1$ are as defined previously.

As shown in SCHEME I, halogenated phenyl aldehyde 1 can be converted to the corresponding nitrile oxide 2 via three steps: formation of the corresponding oxime, halogenation of resultant oxime to generate an intermediate hydroximinoyl halide, and treatment of this intermediate with a suitable base such as triethylamine to afford nitrile oxide 2. The resultant nitrile oxides 2 undergo a 1,3-dipolar cycloaddition with allylic amides (wherein $R_1$ is $C_{1-3}$ alkyl) or carbamates ($R_1$ is O-alkyl) to generate isoxazolines of structure 3 (wherein W is oxygen atom). All these methods are well known to those skilled in the art, and are discussed in further detail in the following references: P. Caramella et al., "1,3-Dipolar Cycloaddition Chemistry", Vol. 1, Chapter 3 of "Nitrile Oxides and Imines", A. Padwa, Ed., John Wiley & Sons, Inc., New York, 1984, pp. 291–392, and references cited therein; C. J. Easton et al., "Advances in Heterocyclic Chemistry", Vol. 60 of "Cycloaddition Reactions of Nitrile Oxides with Alkenes", A. R. Katritzky, Ed., Academic Press, San Diego, 1994, pp. 261–327, and references cited therein; C. Grundmann, et al., *J. Org. Chem.*, 1968, Vol. 33, p. 476; K. C. Liu et al., *J. Org. Chem.* 1980, Vol. 45, p. 3916; T. Mukaiyama et al., *J Am. Chem. Soc.*, 1960, Vol. 82, p. 5339. If desirable, the corresponding thioamide isoxazolines 3 are readily prepared by treatment of carbonyl amide isoxazolines 3 with Lawesson's Reagent in a suitable solvent such as 1,4-dioxane at reflux temperature.

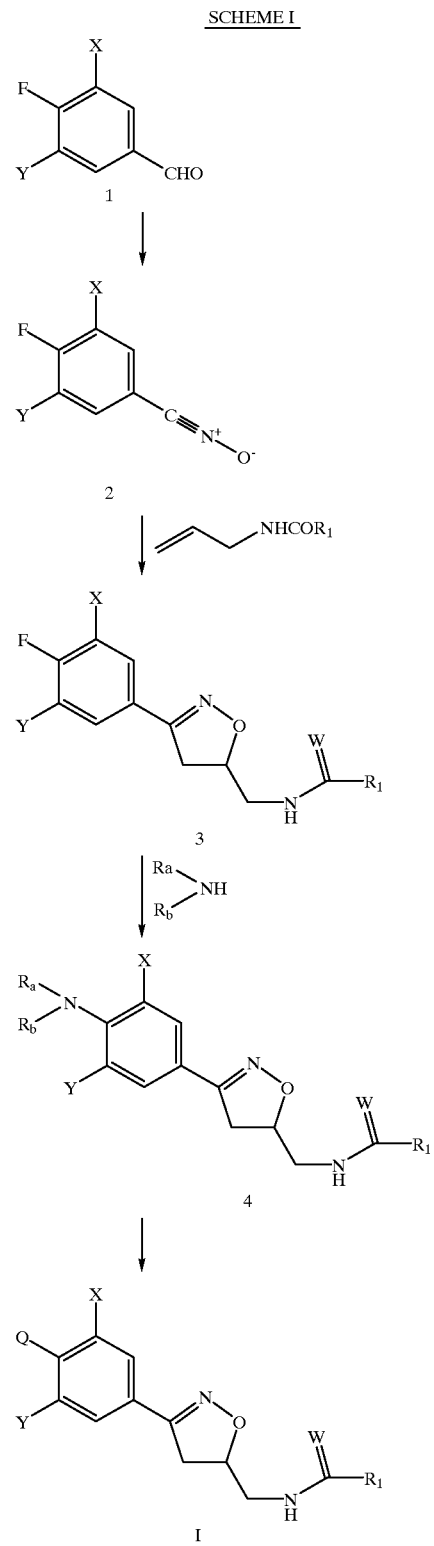

SCHEME I

Treatment of halogenated phenyl isoxazolines 3 with various amines in the presence of a suitable base such as, for example, dipotassium hydrogenphosphate, potassium carbonate, sodium hydride, or excess amines, in a suitable solvent such as, for example, N,N-dimethylformamide, dimethylsulfoxide, tert-butanol, neat amine, etc., at a suitable temperature in the range 40–140° C. and sometimes in a sealed pressure vessel, affords the adduct 4. The compounds 4 are examples of compounds of formula I or are the intermediates that can be elaborated to compounds of formula I of the present invention. For example the hydrazinylphenylisoxazoline 4 (wherein $R_a$ is amino, $R_b$ is hydrogen) can be used to prepare pyrazolyl phenyl isoxazolines and various other heterocyclic phenyl isoxazolines. Similarly, amidomethyl isoxazolines 4 can be converted to the corresponding thioamide products by treatment with Lawesson's Reagent at this stage.

As shown in SCHEME II, the nitrile oxide 2 can be reacted with allyl alcohol to generate 5-(hydroxymethyl) isoxazolines 5. Then, the structure 5 is converted to the corresponding alkylsulfonate or arylsulfonate 6. A representative alkylsulfonyl derivative, the mesylate ($Rc=CH_3$), is prepared by reacting 5 with methanesulfonyl chloride in pyridine/dichloromethane or methanesulfonyl chloride and triethylamine in dichloromethane. Utilization of arylsulfonyl chloride reagents, for example, p-toluenesulfonyl chloride in pyridine or 3-nitrobenzenesulfonyl chloride and triethylamine in dichloromethane, affords aryl sulfonates such as tosylate ($R_c$ is p-tolyl) or nosylate ($R_c$ is 3-nitrophenyl), respectively. The mesylate or nosylate derivative 6 is then converted to the corresponding 5-(aminomethyl) isoxazoline 7 by treatment with aqueous ammonia in a suitable solvent system, for example acetonitrile/isopropanol or tetrahydrofuran/isopropanol, in a sealed reaction vessel, and at a suitable temperature in the range from 40 to 90° C.

SCHEME II

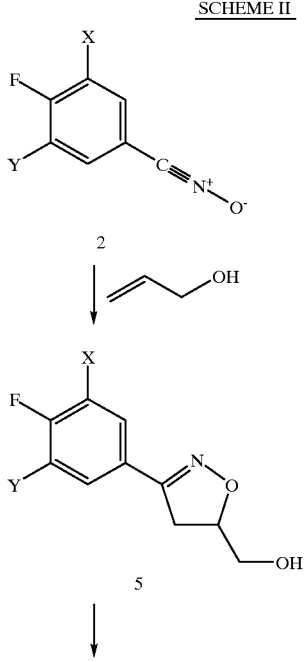

It will be apparent to those skilled in the art that alternative synthetic procedures for the introduction of the requisite aminomethyl side chain are available. For example, the sulfonate 6 can be reacted with an azide source such as sodium or potassium azide in an aprotic solvent such as N,N-dimethylformamide or 1-methyl-2-pyrrolidinone optionally in the presence of a catalyst such as 18-crown-6 at a temperature of 50 to 90° C. to generate the corresponding 5-(azidomethyl) isoxazoline. The azide moiety is then reduced by hydrogenation with a palladium or platinum catalyst in a suitable solvent such as ethyl acetate or methanol to give 7. Alternatively, the azidomethyl intermediate can be reduced to the corresponding amine 7 by a two-step process involving treatment with a trivalent phosphorus compound such as triphenylphosphine in a suitable solvent such as tetrahydrofuran followed by hydrolysis of the resultant iminophosphorane with water. See: M. Vaultier, et al., Tetrahedron Lett., 1983, Vol. 24, p. 763. The amine 7 is then converted to the isoxazoline derivatives 3 by reactions known to those skilled in the art. For example, the amine 7 can be reacted with an acid chloride or anhydride in a basic solvent system such as pyridine or triethylamine/ dichloromethane at a temperature ranging from –30 to 30° C. to provide the acylated compound 3 (wherein W is oxygen atom). Various methods for acylation reactions are discussed further in J. March, "Advanced Organic Chemistry", 3rd ed., John Wiley & Sons, Inc., New York, 1985, pp. 370–375. The corresponding thioamides phenyl isoxazoline 3 (W is sulfur atom) are readily prepared by treatment of amide phenyl isoxazoline with Lawesson's Reagent in a suitable solvent such as 1,4-dioxane at reflux temperature. It will be apparent to those skilled in the art that other carbonyl-containing groups within the scope of this invention can be readily appended to the amine 7 by standard acylation techniques to give additional examples of 3. The remaining synthetic steps which lead structure 3 to the compound of formula I are the similar to that described in SCHEME I.

SCHEME III outlines an alternative reaction procedure which permits synthetic access to selected compounds of formula I of the present invention. It will be apparent to one skilled in the art that the exemplified Q substituent, morpholine or thiomorpholine, is merely representative and that other heterocyclic ring systems are possible. A halogenated benzoate ester of structure 8 (wherein halogen is preferably a fluorine atom) is reacted with morpholine (wherein E is oxygen atom) or thiomorpholine (wherein E is sulfur atom), in the presence of a suitable base such as dipotassium hydrogenphosphate, in an appropriate solvent such as dimethylsulfoxide, and at a suitable temperature in the range from 60 to 100° C., to provide the morpholino adduct 9. The ester moiety of 9 is then reduced to the corresponding benzyl alcohol 10 with an appropriate reducing agent, such as lithium aluminum hydride and the like, in a suitable solvent, for example tetrahydrofuran, and at a suitable temperature in the range from −20 to 0° C. The product alcohol 10 is then oxidized, employing catalytic tetrapropylammonium perruthenate and N-methylmorpholine-N-oxide in dichloromethane, to the corresponding carboxaldehyde 11. The remaining synthetic steps which lead aldehyde 11 through nitrile oxide 12 to morpholino phenylisoxazoline 13 are similar to the procedures described in SCHEME I. Furthermore, in the case where E is sulfur atom, the sulfur atom can be oxidized to provide the corresponding sulfones and sulfoxides, respectively, in an early synthetic step or at the end of synthetic step if desirable. The detailed procedure for this oxidation is discussed in international publication No. WO 97/09328.

Enantiomerically enriched phenylisoxazolines of formula I may be obtained through the racemic phenylisoxazolines 3 or 4 by employing high pressure liquid chromatography (HPLC) over a chiral stationary phase. In a typical separation, the mixture of enantiomers is chromatographed with a 5×50 cm Chiralpak AD column, eluting with heptane/isopropanol/chloroform mixtures as the mobile phase, to provide the individual (R)- or (S)-enantiomer. If desired, the separation of enantiomers can be conducted either on the early intermediates 3 or 4 or on the final product.

Enantiomerically enriched phenylisoxazolines may also be prepared according to procedures outlined in SCHEMES IV and V. As illustrated in SCHEME IV, reaction of nitrile oxides 2 with α,β-unsaturated esters or amides 14 undergoes an asymmetric 1,3-dipolar cycloaddition to provide compound 15. In this reaction, group $R_d$ of compound 14 is a chiral auxiliary used to control the direction of asymmetric induction, and therefore it allows the asymmetric cycloaddition to occur with high steroselectivity.

SCHEME IV

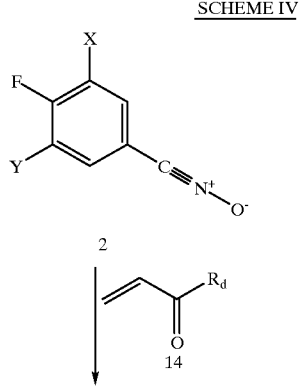

SCHEME III

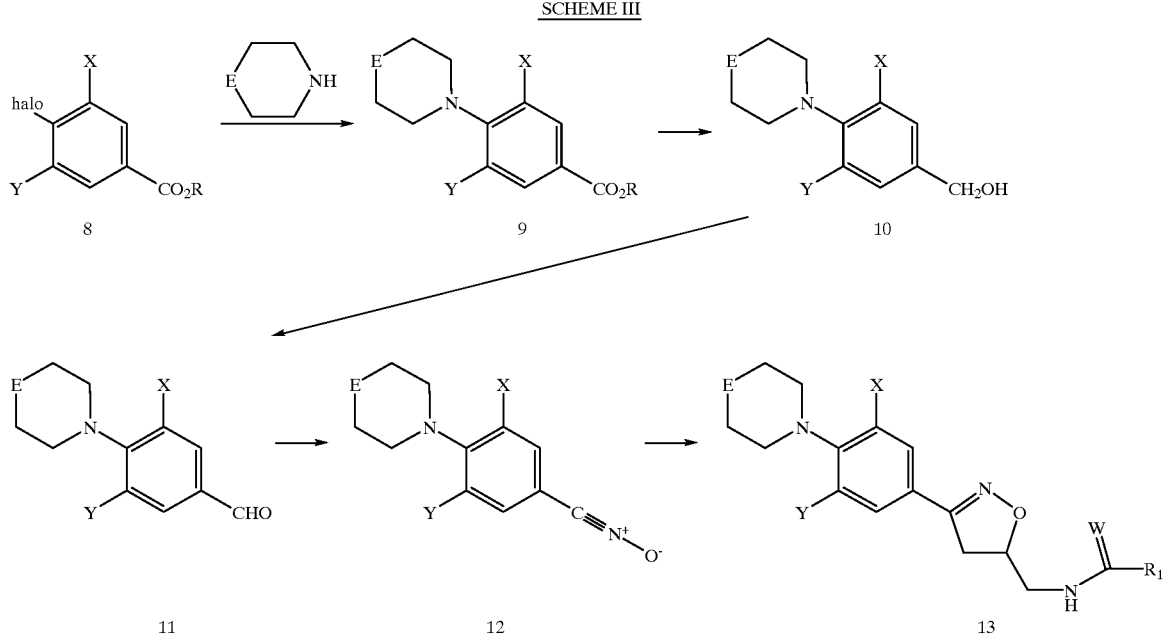

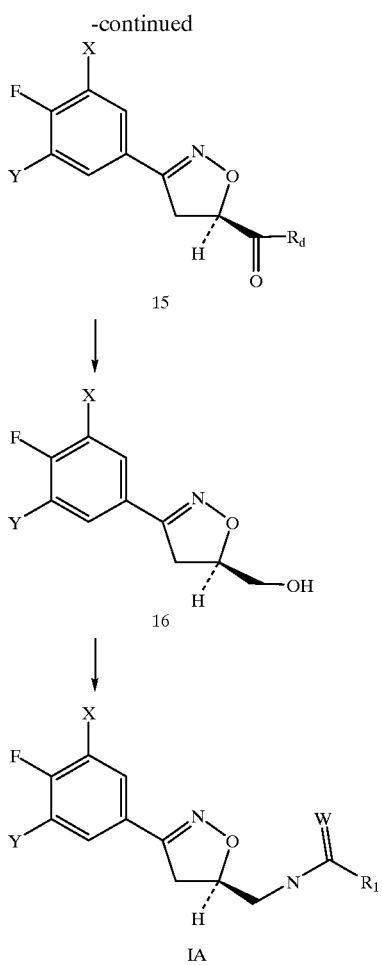

Compound 14 can be prepared from, among the others, Kemp's triacid, Oppolzer's sultam, or chiro-inositol as described in such references as D. P. Curran et al., *J. Am. Chem. Soc.,* 1989, Vol. 111, p. 9238; J. A. Stack, et al., *Tetrahedron,* 1993, Vol. 49, p. 995; D. P. Curran et al., *Tetrahedron Lett.,* 1988, Vol., 29, p. 3555; W. Oppolzer, et al., *Tetrahedron Lett.,* 1991, Vol. 32, p. 4893; T. Akiyama et al., *Tetrahedron Lett.,* 1992, Vol. 33, p. 5763; Y. H. Kim et al., *Tetrahedron Lett.,* 1993, Vol. 34, p. 6063; C. J. Easton et al., "Advances in Heterocyclic Chemistry", Vol. 60 of "Cycloaddition Reactions of Nitrile Oxides with Alkenes", A. R. Katritzky, Ed., Academic Press, San Diego, 1994, pp.261–327, and references cited therein. Use of appropriate chiral auxiliaries to control the steroselectivity of the asymmetric 1,3-dipolar cycloaddition provides access, ultimately, to both enantiomers of 15. For simplicity, only one enantiomer is presented. racemic esters of structural formula 15 (wherein $R_d$ is OMe or OEt) may also be resolved by an enzymatic ester hydrolysis procedure described in S. Yang et al., *Monatsh. Chem.,* 1994, Vol, 125, p. 469.

The enantiomeric cycloadducts 15 may be further purified by recrystallization or chromatography. Treatment of the cycloadducts 15 with a suitable reducing agent such as L-selectride (commercially available) in an appropriate solvent such as tetrahydrofuran then provides the enantiomerically enriched 5-(hydroxymethyl) isoxazolines 16. The remaining synthetic steps which lead 16 to enantiomerically enriched phenylisoxazolines of formula IA are similar to the procedures outlined in SCHEME II.

Alternatively, compound 16 may prepared by treatment of nitrile oxide 2 with an allyl alcohol via a highly enantioselective 1,3-dipolar cycloaddition as shown in SCHEME V.

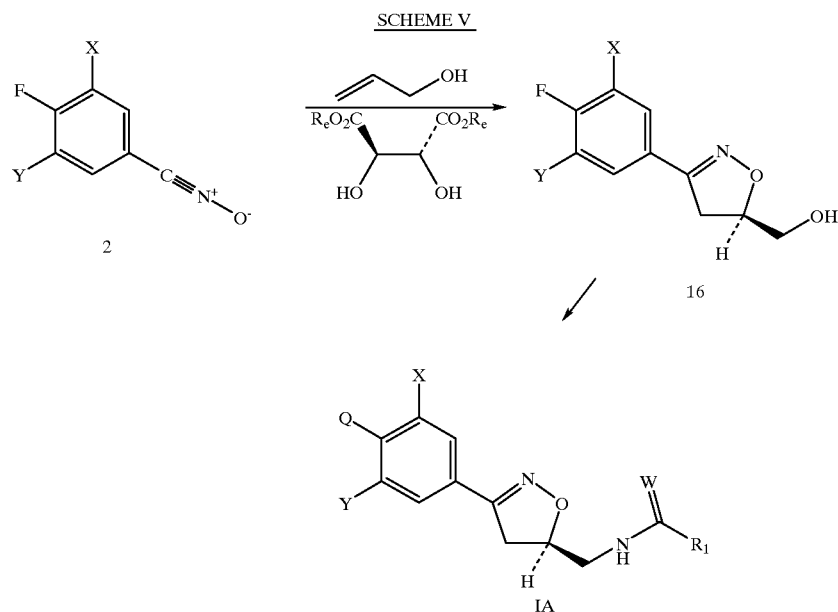

The reaction occurs in the presence of diethylzinc and (R,R)- and (S,S)-tartaric acid esters, preferably, diisopropyl esters, in a suitable solvent such as chloroform or dichloromethane and at a temperature in the range of about −20 to 0° C. See Y. Ukaji et al., Chem. Letters, 1993, p. 1847. The remaining synthetic steps which lead compound 16 to enantiomerically enriched phenylisoxazolines of formula IA are similar to the procedures outlined in SCHEME II.

The pharmaceutical compositions of this invention may be prepared by combining the compounds of formula I of this invention with a solid or liquid pharmaceutically acceptable carrier, and optionally, with pharmaceutically acceptable adjuvants and excipients employing standard and conventional techniques. Solid form compositions include powders, tablets, dispersible granules, capsules and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water, water-propylene glycol, and water-polyethylene glycol systems, optionally containing conventional coloring agents, flavoring agents, stabilizers and thickening agents.

The pharmaceutical composition is provided by employing conventional techniques. Preferably the composition is in unit dosage form containing an effective amount of the active component, that is, the compounds of formula I according to this invention.

The quantity of active component, that is, the compounds of formula I according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

In therapeutic use for treating bacterial infections in humans and other animals that have been diagnosed with bacterial infections, the compounds or pharmaceutical compositions thereof will be administered orally, parenterally, transdermally and/or topically at a dosage to obtain and maintain a concentration, that is, an amount, or blood-level of active component in the animal undergoing treatment which will be antibacterially effective. Generally, such antibacterially effective amount of dosage of active component will be in the range of about 0.1 to about 100 mg/kg, more preferably about 3.0 to about 50 mg/kg of body weight/day. It is to be understood that the dosages may vary depending upon the requirements of the patient, the severity of the bacterial infection being treated, and the particular compounds being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two to four times per day.

These compounds are useful for the treatment of microbial infections in humans and other warm blooded animals by either oral, parenteral, topical, or transdermal administration. In general, the preferred form of administration is orally. Pharmaceutical compositions for parenteral administration will generally contain a pharmaceutically acceptable amount of the compounds according to formula I as a soluble salt (acid addition salt or base salt) dissolved in a pharmaceutically acceptable liquid carrier such as, for example, water-for-injection and a suitably buffered isotonic solution having a pH of about 3.5–6. Suitable buffering agents include, for example, trisodium orthophosphate, sodium bicarbonate, sodium citrate, N-methylglucamine, L(+)-lysine and L(+)-arginine, to name a few. The compounds according to formula I generally will be dissolved in the carrier in an amount sufficient to provide a pharmaceutically acceptable injectable concentration in the range of about 1 mg/ml to about 400 mg/ml. The resulting liquid pharmaceutical composition will be administered so as to obtain the above mentioned antibacterially effective amount of dosage. The compounds of formula I according to this invention are advantageously administered orally in solid and liquid dosage forms.

The compounds of this invention are useful antimicrobial agents, effective against various human and veterinary pathogens, including multiply-resistant staphylococci and streptococci, as well as anaerobic organisms such as bacteroides and *clostridia* species, and acid-resistant organisms such as *Mycobacterium tuberculosis* and *Mycobacterium avium*. Humans or animals infected with such pathogens are readily diagnosed by a physician or veterinarian of ordinary skill.

Antimicrobial activity is tested in vitro using the procedure described in National Committee for Clinical Laboratory Standards. Methods for dilution antimicrobial susceptibility tests for bacteria that grow aerobically are disclosed in the third edition of Approved Standard, NCCLS Document M7-A3, Villanova, Pa., 1993. Minimum inhibitory concentration (MIC) values are determined by an agar dilution method (1) in which the test medium is Mueller Hinton agar (MHA; Difco Laboratories, Detroit, Mich.) supplemented with 1% Supplement C (Difco). Serial two-fold dilutions of each compound are prepared using 1.0 ml volumes of sterile distilled water. To each 1.0 ml aliquot is added 9.0 ml of molten agar medium. The drug-supplemented agar is mixed, poured into 15×100 mm petri dishes, and allowed to solidify and dry at room temperature prior to inoculation. The test cultures are grown aerobically overnight at 35° C. on MHA; streptococcal strains are grown on Trypticase Soy Blood Agar Base EH (Difco) supplemented with 5% defibrinated sheep blood (BBL, Becton Dickinson Company, Cockeysville, Md.). Colonies are harvested with a sterile swab, and cell suspensions are prepared in Trypticase Soy Broth (TSB; Becton Dickinson Company) to equal the turbidity of a 0.5 McFarland standard. A 1:19 dilution of the suspension is made in TSB; this diluted suspension constituted the inoculum for the assay. The plates containing the drug-supplemented agar are inoculated with a 0.001 ml drop of the cell suspensions using a Steers replicator (Melrose Machine Shop, Woodlyn, Pa.), yielding approximately $10^4$–$10^5$ cells per spot. The plates are incubated aerobically at 35° C. for 18 hours and the MIC is read as the lowest concentration of drug that inhibited visible growth of the organism. The growth of a single colony is considered to be negative. The data are shown in TABLE 1.

TABLE 1

In Vitro Activity (μg/mL) of Compounds Against
Staphylococcus aureus UC ® No. 9213,
Staphylococcus aureus UC ® No. 12673,
Enterococcus faecalis UC ® No. 9217
and Streptococcus Pneumoniae UC ® No. 9912.

| Example No. | S. aureus UC9213 | S. aureus UC12673 | E. faecallis UC9217 | S. pneumoniae UC9912 |
|---|---|---|---|---|
| 1 | 16 | 16 | >16 | 4 |
| 2 | 16 | 8 | 16 | 4 |
| 3 | >16 | >16 | 16 | 0.5 |
| 4 | 8 | 8 | 8 | 2 |
| 5 | 8 | 8 | 16 | 4 |
| 6 | 4 | 4 | 8 | 2 |
| 7 | 4 | 4 | 4 | 1 |
| 8 | 8 | 4 | 8 | 2 |
| 9 | 16 | 16 | 8 | 0.5 |
| 10 | 16 | 8 | 8 | 2 |
| 11 | 4 | 4 | 8 | 2 |
| 12 | 2 | 2 | 4 | 0.5 |
| 13 | 2 | 2 | 4 | 1 |
| 14 | 2 | 2 | 4 | 0.5 |
| 15 | 0.5 | 0.5 | 1 | 0.25 |
| 16 | 1 | 0.5 | 1 | 0.25 |
| 17 | 1 | 0.5 | 1 | <0.125 |
| 18 | 1 | 1 | 1 | 0.5 |
| 19 | <0.125 | <0.125 | 0.25 | <0.125 |
| 20 | 2 | 1 | 2 | 0.5 |
| 21 | 8 | 8 | 8 | 2 |
| 22 | 2 | 4 | 2 | 0.5 |
| 23 | 4 | 4 | 4 | 1 |
| 24 | 4 | 4 | 8 | 1 |
| 25 | 4 | 4 | 4 | 0.25 |
| 26 | 2 | 2 | 2 | 0.5 |
| 27 | 2 | 1 | 2 | 0.5 |
| 28 | 8 | 8 | 8 | 2 |
| 29 | 4 | 4 | 8 | 2 |
| 30 | 1 | 1 | 1 | 0.25 |
| 31 | 4 | 4 | 4 | 1 |

The compounds, processes and uses of the present invention will be better understood in connection with the following examples, which are intended as an illustration of and not a limitation upon the scope of the invention. Both below and throughout the specification, it is intended that citations to the literature are expressly incorporated by reference herein.

EXAMPLE 1

Preparation of (±)-N-[[4,5-Dihydro-3-[4-(1H-imidazol-1-yl)phenyl]-5-isoxazolyl]methyl]acetamide

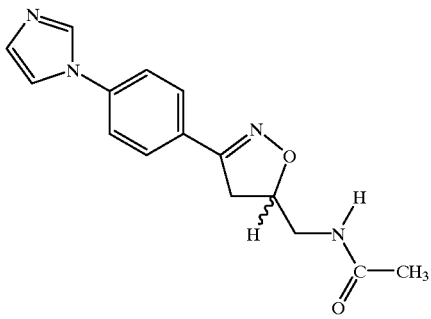

Step 1: To a flask containing 4-fluorobenzaldehyde (2.00 g) and hydroxylamine hydrochloride (1.23 g) in ethanol (30 mL) and ice (40 mL) at 4° C. is added NaOH (50% (w/w), 3.22 mL). The reaction is stirred for 3 hours, neutralized to pH=6.0, and extracted with $CH_2Cl_2$ (3×100 mL). The organic extracts are combined, washed with saline (50 mL), dried over sodium sulfate, concentrated in vacuo to give 4-fluorobenzaldoxime, mp 85–86° C.

Step 2: To a flame dried flask containing 4-fluorobenzaldoxime (1.00 g) in DMF (100 mL) is added N-chlorosuccinimide (1.70 g) slowly at 0° C. The reaction is warmed to 50° C. for 3 hours, poured over ice, diluted with $H_2O$(100 mL), and extracted with EtOAc (150 mL). The organic phase is washed with $H_2O$ (5×100 mL), saline (100 mL), dried over sodium sulfate, concentrated in vacuo to give a quantitative yield of 4-fluoro-N-hydroxy-benzenecarboximidoyl chloride. To a flask containing 4-fluoro-N-hydroxy-benzenecarboximidoyl chloride (1.25 g) and allyl acetamide (780 mg) in methylene chloride (75 mL) at 0° C. under an inert atmosphere is added triethylamine (3.05 mL, 21.60 mmol). The reaction is slowly warmed to ambient temperature, stirred 20 hours, quenched with water (100 mL), and extracted with methylene chloride (3×100 mL). The organic extracts are combined, washed with saline (50 mL), dried over sodium sulfate, concentrated in vacuo and chromatographed on silica gel (230–400 mesh, 200 mL), eluting with chloroform/methanol (99/1). The appropriate fractions are combined ($R_f$=0.26, TLC, chloroform/methanol, 95/5) and concentrated in vacuo to give (±)-N-[[4,5-dihydro-3-(4-fluorophenyl)-5-isoxazolyl]methyl]acetamide, mp 167–168° C.

Step 3: To a flame dried flask at 0° C. is added DMF (10 mL) and 60% sodium hydride (0.09 g). Imidazole (0.16 g) is added and the mixture warmed to room temperature. The (±)-N-[[4,5-dihydro-3-(4-fluorophenyl)-5-isoxazolyl]methyl]acetamide (500 mg, 2.12 mmol) is added and the mixture heated to 110° C. for 3 days under nitrogen. The reaction progress is monitored by TLC (product $R_f$ 0.10 with 95:5 $CH_2Cl_2$/MeOH). After cooling to ambient temperature, water (5 mL) is added. The mixture is transferred to a separator funnel and extracted with EtOAc (10×). The organic extracts are dried over sodium sulfate, filtered and concentrated in vacuo. Purification on silica gel (200 mL) chromatography, (96:4 $CH_2Cl_2$/MeOH), affords 0.53 g of the title compound, mp 152–154° C.

EXAMPLE 2

Preparation of (±)-N-[[4,5-Dihydro-3-[4-[4-(hydroxyacetyl)-1-piperazinyl]phenyl]-5-isoxazolyl]methyl]acetamide

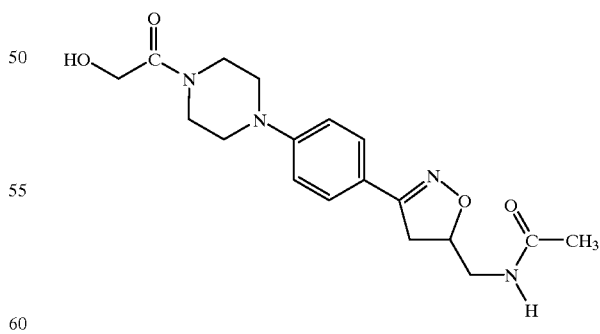

Step 1: A resealable tube containing (+/−)-N-[[4,5-dihydro-3-(4-fluorophenyl)-5-isoxazolyl]methyl]acetamide (500 mg, 2.12 mmol) and piperazine (5.00 g) is heated to 140–150° C. for 24 hours. The reaction vessel is cooled to room temperature and the mixture diluted with $CH_2Cl_2$ (150 mL), brine, and 5–10% MeOH. The organic phase is separated and the aqueous phase extracted (3×50 mL CH$_2$Cl$_2$). The combined organic phases are dried over sodium sulfate, concentrated in vacuo, and chromatographed over silica gel, eluting with 90:10 CHCl$_3$/MeOH, 0.5% NH$_4$OH. Appropriate fractions are combined (R$_f$=0.29, TLC, 90:10 CHCl$_3$/MeOH with drops of NH$_4$OH) and concentrated in vacuo to give 0.365 g of the piperazine adduct, with MS (ESI+) for C$_{16}$H$_{22}$N$_4$O$_2$ m/z 303.3 (M+H)$^+$.

Step 2: To a flask containing (+/−)-N-[[4,5-dihydro-3-[4-(1-piperazinyl)phenyl]-5-isoxazolyl]methyl]acetamide (340 mg) in methylene chloride (5 mL) and triethylamine (0.31 mL) is added acetoxyacetyl chloride (0.16 mL) at 0° C. under an inert atmosphere. The reaction is warmed to ambient temperature, stirred for 2 hours and concentrated in vacuo. The residue is dissolved in methanol (10 mL) and potassium carbonate (460 mg) is added. The reaction is stirred fifteen hours, concentrated in vacuo, and chromatographed on silica gel (230–400 mesh, 100 mL), eluting with chloroform/methanol (96/4). The appropriate fractions are combined (R$_f$=0.07, TLC, chloroform/methanol, 95/5) and concentrated in vacuo to give the title compound, mp 187–190° C.

EXAMPLE 3

Preparation of (±)-N-[[3-[3-Fluoro-4-(1-piperazinyl) phenyl]-4,5-dihydro-5-isoxazolyl]methyl]acetamide

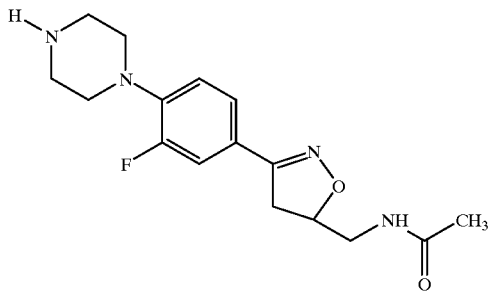

Step 1: 3,4-Difluoro-benzaldehyde (25 g) is dissolved in 75 ml 95% ethanol in a 500 ml one neck round bottom flask. The solution is treated successively with hydroxylamine hydrochloride (14.7 g) in 14 ml water and sodium hydroxide (10.6 g) in 20 ml water (exotherm). The reaction is stirred over the weekend, poured into 300 ml ice, and the white solid is collected. The solid is washed with water, is dissolved in chloroform, and is dried over anhydrous magnesium sulfate. The dried organics are concentrated in vacuo to provide 24.5 g (89%) of 3,4-difluorobenzoxime as a white solid, mp 75–77° C.

Step 2: 3,4-Difluoro-benzoxime (58.4 g) is dissolved in 250 ml dimethylformamide in a flame dried 1,000 ml three neck round bottom flask under nitrogen. The solution is treated with N-chloro-succinimide (8 g) and the reaction is initiated by bubbling in 20 ml of the vapor from the head space of a gallon of 12 N hydrochloric acid. The reaction is allowed to exotherm to 40° C. and is maintained at that temperature via a water bath and the controlled addition of the remaining N-chloro-succinimide (46.6 g). The reaction is stirred 2 hours at room temperature, is poured into ice water and is extracted with 3×300 ml diethyl ether. The combined organics are washed with 4×250 ml 50% saturated sodium chloride, are dried over anhydrous magnesium sulfate, and are concentrated in vacuo to give 68.8 g (96%) of 3,4-difluoro-benzohydroximinoyl chloride as a pale yellow solid.

Step 3: 3,4-Difluoro-benzohydroximinoyl chloride (68.8 g) is combined with N-allyl acetamide (33.8 g) in 1,300 ml diethyl ether in a 2,000 ml three neck round bottom flask under nitrogen equipped with a mechanical stirrer. The solution is treated dropwise with triethylamine (62.5 ml) in 100 ml diethyl ether (exotherm to gentle reflux) and the reaction is stirred 20 hours at room temperature. The suspension is diluted with 750 ml ethyl acetate and is washed with 2×500 ml 50% saturated sodium chloride. The organics are dried over anhydrous magnesium sulfate and are concentrated in vacuo to a yellow pasty solid. The crude material is triturated with 250 ml diethyl ether on the rotary evaporator at 40° C. until about 50 ml had distilled (no vacuum). The mixture is cooled, the solid is collected, washed with cold diethyl ether, and is dried to afford 71 g (82%) of 5-(acetamidomethyl)-3-(3,4-difluorophenyl) isoxazoline as a white solid. An analytical sample is obtained via chromatography over silica gel (230–400 mesh), eluting with 3% methanol/dichloromethane, mp 136–137° C.

Step 4: 5-(Acetamidomethyl)-3-(3,4-difluorophenyl) isoxazoline (4.0 g) is combined with potassium carbonate (2.8 g) and piperazine (13.6 g) a 48 ml screw cap pressure tube under nitrogen. The reaction is warmed to 140° C. for 3 hours, is poured hot into 200 ml ice with a water rinse. The mixture is extracted with 3×50 ml chloroform, the organics are dried over anhydrous potassium carbonate, and are concentrated in vacuo to give a yellow paste. The paste is washed with diethyl ether to afford 4.5 g of a pale tan solid. The crude material is chromatographed over 200 g silica gel (230–400 mesh), eluting with 11% methanol/ dichloromethane +1% concentrated ammonium hydroxide while collecting 22 ml fractions. Fractions 29–50 are combined and concentrated to provide 3.65 g of the title compound as an off-white solid, mp 160–161° C.

EXAMPLE 4

Preparation of (±)-N-[[3-[3-Fluoro-4-[4-(hydroxyacetyl)-1-piperazinyl]phenyl]-4,5-dihydro-5-isoxazolyl]methyl]acetamide

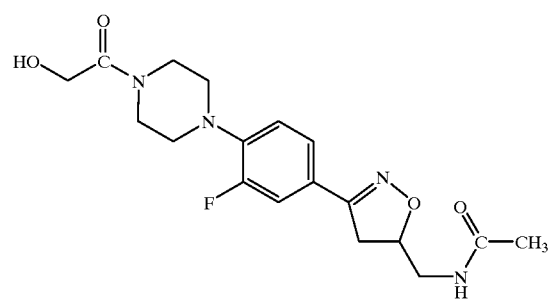

A mixture of Example 3 (1.73 g) and sodium bicarbonate (1.13 g, 13.5 mmol) in dry THF (104 mL) at 0° C. is treated with acetoxyacetyl chloride (811 mg, 5.9 mmol) by syringe and warmed to ambient temperature overnight. After 18 hours, TLC analysis (8% CH$_3$OH/CH$_2$Cl$_2$) indicated the starting material is consumed. To the mixture is added methanol (75 mL) and water (20 mL) and potassium carbonate (750 mg). After 2 hours, TLC analysis (8% CH$_3$OH/CH$_2$Cl$_2$) indicates the second step is to be completed. The mixture is adjusted to neutral pH by addition of 2N HCl, extracted with CH$_2$Cl$_2$ (3×50 mL), dried over Na$_2$SO$_4$, filtered and concentrated under reduced pressure to give 2.02 g (99%) of the title compound as a white solid with $^1$H NMR (CDCl$_3$, 400 MHz) d 7.42, 7.30, 6.93, 5.91, 4.85, 4.22, 3.86, 3.52, 3.35, 3.16, 3.06, 1.99.

EXAMPLE 5

Preparation of (±)-N-[[3-[3-Fluoro-4-(1-pyrrolidinyl)phenyl]-4,5-dihydro-5-isoxazolyl]methyl]acetamide

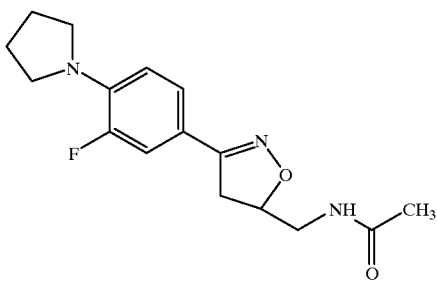

Example 3 (254 mg) is combined with potassium carbonate (175 mg) in 1.5 ml pyrrolidine in a 15 ml screw cap pressure tube under nitrogen. The reaction is warmed to 135° C. for 1 hour, is cooled to room temperature, and the volatiles are removed in vacuo. The residue washed with dichloromethane, is filtered, and the filtrate is concentrated in vacuo to an off-white solid which is washed with diethyl ether and is dried to give 238 mg of the title compound as an off-white solid, mp 141–143° C.

EXAMPLE 6

Preparation of (±)-N-[[3-[3-Fluoro-4-(1H-imidazol-1-yl)phenyl]-4,5-dihydro-5-isoxazolyl]methyl]acetamide

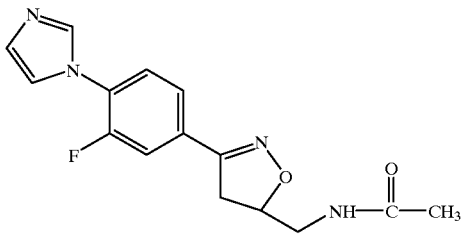

Imidazole (150 mg) is dissolved in 3 ml dimethylformamide in a 25 ml one neck round bottom flask under nitrogen. The solution is cooled to 0° C., is treated with 60% sodium hydride (88 mg), and the mixture is stirred 20 minutes at room temperature. The solution is treated with Example 3 (508 mg), and the reaction is stirred 6 hours at 75° C. The reaction is cooled, the dimethylformamide is removed under a stream of nitrogen, and the residue is washed with water and is dried to give an off-white solid. The crude material is chromatographed over 25 g silica gel (230–400 mesh), eluting with 5% methanol/dichloromethane while collecting 5 ml fractions. Fractions 33–69 are combined and concentrated to give 347 mg of the title compound as a white solid, mp 165–166° C.

EXAMPLE 7

Preparation of (±)-N-[[3-[4-(4-Cyano-1H-pyrazol-1-yl)-3-fluorophenyl]-4,5-dihydro-5-isoxazolyl]methyl]acetamide

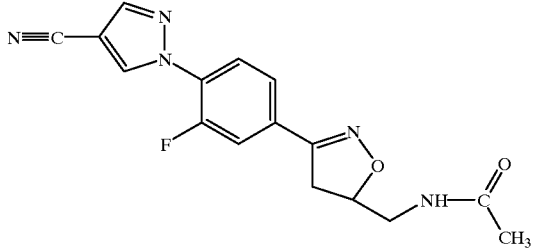

Step 1: The final product of Example 3 (5.08 g) is combined with hydrazine hydrate (9.7 ml) in a 48 ml screw cap pressure tube under nitrogen. The reaction is warmed to 130° C. for 4 hours, is cooled to room temperature, and is diluted with 20 ml 50% saturated sodium bicarbonate. The solids are collected, are washed with 2×10 ml water, and the solid is dissolved in 150 ml methanol. The solution is concentrated to dryness. The solid is redissolved in 20 ml methanol/300 ml acetonitrile, the insoluble material is removed by filtration, and the solution is treated with acetic anhydride (1.7 ml). The suspension is stirred for 1 hour at room temperature. The solid is collected, washed with diethyl ether, and is dried to provide 2.66 g (50%) of the hydrazine adduct as a white solid, mp 200–201° C.

Step 2: The product of Step 1 (443 mg) is combined with sodium-3,3-dimethoxy-propionitrile-2-formylate (302 mg) in 8 ml absolute ethanol in a 25 ml one neck round bottom flask under nitrogen. The suspension is treated with 1 ml concentrated hydrochloric acid and the reaction is stirred at 60° C. for 30 minutes.

The reaction is cooled, the volatiles are removed in vacuo, and the residue is diluted with water and saturated sodium bicarbonate. The yellow solid is collected, washed with water and is dried to give a yellow solid. The crude material is chromatographed over 25 g silica gel (230–400 mesh), eluting with 5% methanol/dichloromethane while collecting 5 ml fractions. Fractions 9–30 are combined and concentrated to give 408 mg (81%1) of the title compound as a white solid, mp 169–171° C.

EXAMPLE 8

Preparation of (±)-N-[[3-[4-(4-Cyano-1H-1,2,3-triazol-1-yl)-3-fluorophenyl]-4,5-dihydro-5-isoxazolyl]methyl]acetamide

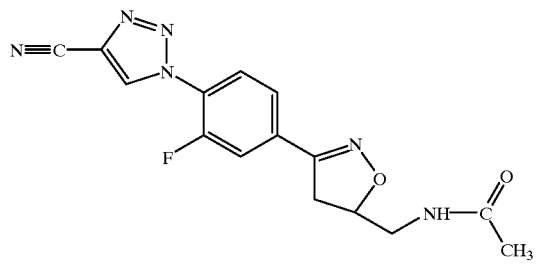

Step 1: The hydrazine derivative (Step 1, Example 7) (1.65 g) is combined with 12N hydrochloric acid (2.5 ml) in 12 ml water and 6 ml methanol in a 50 ml one neck round bottom flask under nitrogen at −10° C. The suspension is treated slowly dropwise with sodium nitrite (432 mg) in 3 ml water and the reaction is stirred 1 hour at −10° C. The reaction is quenched into 100 ml saturated sodium bicarbonate and is extracted with 4×25 ml ethyl acetate. The organics are dried via filtration through anhydrous potassium carbonate and are concentrated in vacuo to a yellow solid. The crude material is chromatographed over 60 g silica gel (230–400 mesh) eluting with 3% methanol/dichloromethane while collecting 9 ml fractions. Fractions 15–42 are combined and concentrated to afford 1.22 g (72%) of the azide as a tan solid, mp 161–162° C.

Step 2: 5-Acetamido-3-(4-azido-3-fluorophenyl)isoxazoline (277 mg) is combined with methyl propiolate (0.356 ml) in 3 ml benzene in a screw cap pressure tube under nitrogen. The reaction is warmed to 105° C. for 1 hour, is cooled to room temperature, and is washed into a recovery flask with ethyl acetate. The volatiles are removed in vucuo. The crude material is recrystallized from ethyl acetate to provide 252 mg (70%/) of 5-acetamido-3-(4-(4-carbomethoxy-1,2,3-triazol-1-yl)-3-fluorophenyl)isoxazoline as an off-white solid, mp 221° C.

Step 3: 5-Acetamido-3-(4-(4-carbomethoxy-1,2,3-triazol-1-yl)-3-fluorophenyl)isoxazoline (890 mg) is combined with 6 ml concentrated ammonium hydroxide and 6 ml acetonitrile in a 48 ml screw cap pressure tube. The reaction is slowly warmed to 75° C. and is stirred 2 hours. The reaction is cooled to room temperature, the volatiles are removed in vacuo, and the residue is washed with water. The solid is air dried to afford 708 mg of analytically pure 5-acetamido-3-(4-(4-carboxamido-1,2,3-triazol-1-yl)-3-fluorophenyl) isoxazoline as a pale tan solid, mp 270–272° C.

Step 4: 5-Acetamido-3-(4-(4-carboxamido-1,2,3-triazol-1-yl)-3-fluorophenyl)isoxazoline (475 mg) is suspended in 15 ml dichloromethane in a 50 ml one neck round bottom flask under nitrogen. The solution is treated with pyridine (0.366 ml) followed by trifluoroacetic anhydride (0.290 ml) dropwise in 10 ml dichloromethane. The reaction is stirred 4 hours at room temperature and then is concentrated. The residue is stirred vigorously with 1×50 ml saturated sodium bicarbonate for 1 hour. The precipitate is collected, washed with water, and is dried to give 480 mg of crude solid. The crude material is chromatographed over 25 g silica gel (230–400 mesh) eluting with 7% methanol/dichloromethane while collecting 9 ml fractions. Fractions 12–33 are combined and concentrated to afford 260 mg of the title compound as a white solid, mp 180–181° C.

EXAMPLE 9

Preparation of (±)-N-[[3-[3,5-Difluoro-4-(1-piperazinyl)phenyl]-4,5-dihydro-5-isoxazolyl]methyl]acetamide

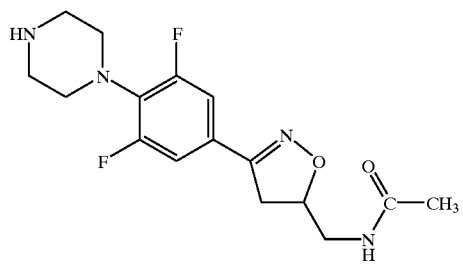

Step 1: A mixture of 3,4,5-trifluorobenzaldehyde (3.0 g) in 10 mL 1:1 ethanol-water is cooled to 0° C. and then treated with hydroxylamine hydrochloride (1.43 g) followed by 50% aqueous sodium hydroxide solution at a rate keeping the mixture at or below 20° C. After 1.5 hours, TLC analysis (2% CH₃OH/CH₂Cl₂) revealed the reaction to be complete. The solution is diluted with 10 mL water and acidified to pH 6 by addition of concentrated HCl resulting in a cloudy mixture. The mixture is extracted with EtOAc (3×15 mL), dried over Na₂SO₄, filtered and concentrated under reduced pressure to give a quantitative yield of the oxime derivative as a white solid, mp 83–85° C.

Step 2: A solution of the oxime derivative of Step 1 (2.25 g) in dry DMF (11 mL) is treated with N-chlorosuccinimide (1.72 g) in several portions. An exotherm up to 60° C. is observed. Heating at 50° C. is maintained for 1 hour at which time TLC analysis (2% CH₃OH/CH₂CL₂) indicated the starting material is consumed. The mixture is diluted with EtOAc (40 mL), extracted with water (4×50 mL), dried over Na₂SO₄, filtered and concentrated under reduced pressure to give the crude hydroximinoyl chloride derivative. The crude product is not purified further.

Step 3: A solution of the hydroximinoyl product of Step 2 (2.68 g) in dry CH₂Cl₂ (120 mL) is treated with N-allyl acetamide (1.27 g) and the mixture is cooled to 0° C. Triethylamine (1.3 g) is added dropwise and the mixture is allowed to warm to ambient temperature. After 2 hours, TLC analysis (1% CH₃OH/CH₂CL₂) revealed the reaction to be complete. The mixture is extracted with water (3×50 mL), dried over Na₂SO₄, filtered and concentrated under reduced pressure to give 3.05 g (88%) of the title compound as a yellow solid. Recrystal-lization from 10% hexane/EtOAc gives 1.77 g (51%) of 5-(acetamidomethyl)-3-(3,4,5-trifluorophenyl)isoxazoline as a white solid with mp 136–137° C.

Step 4: A mixture of (±)-5-(acetamidomethyl)-3-(3,4,5-trifluorophenyl)isoxazoline (600 mg), piperazine (1.90 g) and dibasic potassium phosphate (1.15 g) is * slurred in dry DMSO (2.5 mL) and heated at 90° C. After 60 hours, the mixture is cooled to ambient temperature and TLC analysis (8% CH₃OH/CH₂Cl₂) indicated the reaction is complete. The waxy mixture is dissolved in water (40 mL), adjusted to pH 6 by addition of 1N HCl and extracted with EtOAc (3×30 mL) and CH₂Cl₂ (3×30 mL). The organic solutions are combined, dried over Na₂SO₄, filtered and concentrated under reduced pressure. The crude product is chromatographed over silica (radial chromatography, 4 mm plate) eluting with 2% CH₃OH/CH₂Cl₂ and 1%NH₄OH/5/ CH₃OH/CH₂Cl₂ to give 359 mg of the title compound as a white solid, mp 147–148° C.

EXAMPLE 10

Preparation of (±)-N-[[3-[3,5-Difluoro-4-(4-morpholinyl)phenyl]-4,5-dihydro-5-isoxazolyl]methyl]acetamide

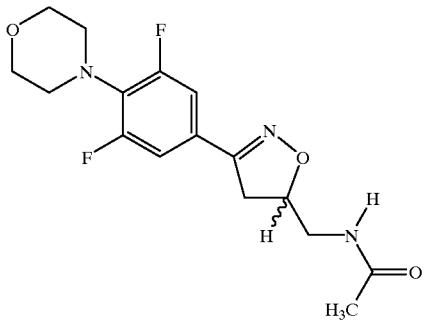

Step 1: To a flame dried flask containing ethyl (3,4,5-trifluorophenyl)acetate (4.45 g) in DMSO (100 mL) is added $K_2HPO_4$ (15.19 g) and morpholine (2.09 g). The mixture is heated to 75° C. for 15 hours. The reaction is diluted with ethyl acetate (100 mL) and washed with $H_2O$ (6×100 mL), washed with saline (50 mL), dried over sodium sulfate, concentrated in vacuo and chromatographed on silica gel (230–400 mesh, 200 mL), eluting with hexane/ethyl acetate (95/5). The appropriate fractions are combined ($R_f$=0.53, TLC, hexane/ethyl acetate, 75/25) and concentrated in vacuo to give ethyl 3,5-difluoro-4-(4-morpholino)benzoate, MS (ESI+) for $C_{13}H_{15}NO_3F_2$ m/z 272.2 (M+H)$^+$.

Step 2: To a flame dried flask containing ethyl 3,5-difluoro-4-(4-morpholino)benzoate (5.00 g) in THF (40 mL) at –10° C. is added LAH (37 mL, 1M in THF) slowly keeping the temperature <25° C. The reaction is cooled to 0° C., stirred 1 hour, and quenched with $H_2O$ (4 mL), NaOH (1.4 mL, 1N), and $H_2O$ (4.2 mL) slowly. The reaction is diluted with ethyl acetate (100 mL), filtered through celite, and concentrated in vacuo to give 4.13 g (98%) of semi-pure 3,5-difluoro-4-(4-morpholino)benzyl alcohol. To a flame dried flask containing 4 Å sieves (3.07 g) in $CH_2Cl_2$ (50 mL) is added N-methylmorpholine-N-oxide (3.07 g), 3,5-difluoro-4-(4-morpholino)benzyl alcohol (4.00 g) and tetrapropylammonium perruthenate (TPAP) (310 mg). The reaction is stirred for 1.5 hours, filtered through silica gel (70–230 mesh, 50 mL), concentrated in vacuo and chromatographed on silica gel (230–400 mesh, 200 mL), eluting with hexane/ethyl acetate (85/15). The appropriate fractions are combined ($R_f$=0.43, TLC, hexane/ethyl acetate, 75/25) and concentrated in vacuo to give 3,5-Difluoro-4-(4-morpholino) benzaldehyde, mp 63–65° C.

Step 3: To a flask containing 3,5-difluoro-4-(4-morpholino) benzaldehyde (3.10 g, 13.64 mmol) and hydroxylamine hydrochloride (1.04 g) in ethanol (75 mL) and ice (50 mL) at 4° C. is added NaOH (50% (w/w), 2.73 mL). The reaction is stirred for 2 hours, neutralized to pH=6.0, and extracted with $CH_2Cl_2$ (3×50 mL). The organic extracts are combined, washed with saline (50 mL), dried over sodium sulfate, concentrated in vacuo to give 3.27 g (99%) of semi-pure 3,5-difluoro-4-(4-morpholino)benzaldehydroxime as a pale yellow solid, MS (ESI+) for $C_{11}H_{12}N_2O_2F_2$ m/z 243.1 (M+H)$^+$.

Step 4: To a flame dried flask containing 3,5-difluoro-4-(4-morpholino)benzaldehydroxime (3.25 g) in DMF (50 mL) is added N-chlorosuccinimide (2.24 g) slowly at 0° C. The reaction is warmed to 50° C. for 4 hours, poured over ice, diluted with $H_2O$ (100 mL), and extracted with EtOAc (200 mL). The organic phase is washed with $H_2O$ (6×50 mL), saline (100 mL), dried over sodium sulfate, concentrated in vacuo to give 3.71 g (100%) of 3,5-difluoro-4-(4-morpholino)-N-hydroxy-benzenecarboximidoyl chloride.

To a flask containing 3,5-difluoro-4-(4 -morpholino)-N-hydroxy-benzenecarboximidoyl chloride (3.71 g) and allyl acetamide (1.33 g) in methylene chloride (75 mL) at 0° C. under an inert atmosphere is added triethylamine (2.06 mL). The reaction is slowly warmed to ambient temperature, stirred 20 hours, quenched with water (100 mL), and extracted with methylene chloride (3×100 mL). The organic extracts are combined, washed with saline (50 mL), dried over sodium sulfate, concentrated in vacuo and chromatographed on silica gel (230–400 mesh, 250 mL), eluting with chloroform/methanol (99/1). The appropriate fractions are combined ($R_f$=0.30, TLC, chloroform/methanol, 95/5) and concentrated in vacuo to give the title compound, mp 145–149° C.

EXAMPLE 11

Preparation of (–)-N-[[3-[3-Fluoro-4-(1-pyrrolidinyl)phenyl]-4,5-dihydro-5-isoxazolyl]methyl]acetamide

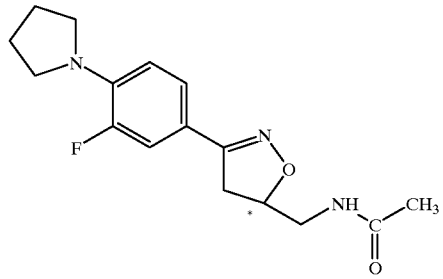

(–) enantiomer

Step 1: (±)-5-(Acetamidomethyl)-3-(3,4-difluorophenyl) isoxazoline (Step 3, Example 3) is resolved into its individual enantiomers by preparative chiral HPLC, employing a Chiralpak AD column and eluting with isopropanol/heptane, to provide the (–)-enantiomer.

Step 2: (–)-5-(Acetamidomethyl)-3-(3,4-difluorophenyl) isoxazoline (762 mg) is combined with 2.5 ml pyrrolidine in a 15 ml screw cap pressure tube under nitrogen. The reaction is warmed to 130° C. for 2 hours, is cooled to room temperature, and is diluted with 20 ml chloroform. The organics are washed with 1×25 ml 50% saturated sodium bicarbonate, are dried over anhydrous potassium carbonate, and are concentrated in vacuo to an off-white solid. The crude material is chromatographed over 50 g silica gel (230–400 mesh), eluting with 5% methanol/dichloromethane while collecting 5 ml fractions. Fractions 12–31 are combined and concentrated to afford a white solid which is washed with diethyl ether and is dried to give 761 mg (83%) of the title compound as a white solid, mp 165–166° C., $[\alpha]^{25}_D$ –57° (c 0.76).

EXAMPLE 12

Preparation of (−)-N-[[3-[3-Fluoro-4-(1H-pyrrol-1-yl)phenyl]-4,5-dihydro-5-isoxazolyl]methyl]acetamide

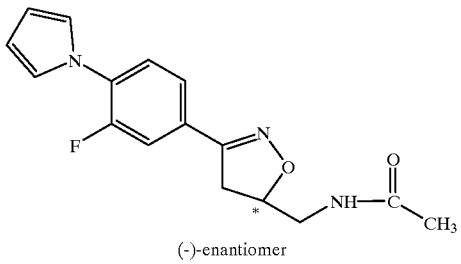

(−)-enantiomer

Pyrrole (0.299 ml) is dissolved in 7 ml dimethylformamide in a 25 ml one neck round bottom flask under nitrogen. The solution is cooled to 0° C., is treated with 60% sodium hydride (132 mg) and the mixture is stirred 20 minutes at room temperature. The solution is treated with (−)-5-(acetamidomethyl)-3-(3,4-difluorophenyl)-isoxazoline (Step 1, Example 11) (763 mg), and the reaction is stirred 2 hours at 50–60° C. The reaction is cooled, the dimethylformamide is removed under a stream of nitrogen, and the residue is washed with water followed by diethyl ether and is dried to give an off-white solid. The crude material is chromatographed over 25 g silica gel (230–400 mesh), eluting with 5% methanol/dichloromethane while collecting 5 ml fractions. Fractions 13–30 are combined and concentrated to give 520 mg (58%) of the title compound as a white solid, mp 176–177° C., $[\alpha]^{25}_D$ −73° (c 0.75).

EXAMPLE 13

Preparation of (−)-N-[[3-[3-Fluoro-4-(1H-imidazol-1-yl)phenyl]-4,5-dihydro-5-isoxazolyl]methyl]acetamide

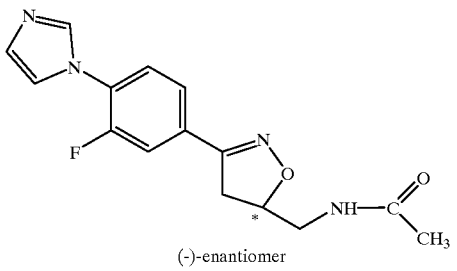

(−)-enantiomer

Imidazole (225 mg) is dissolved in 5 ml dimethylformamide in a 25 ml one neck round bottom flask under nitrogen. The solution is cooled to 0° C., is treated with 60% sodium hydride (132 mg), and the mixture is stirred 20 minutes at room temperature. The solution is treated with (−)-5-(acetamidomethyl)-3-(3,4-difluorophenyl)-isoxazoline (Step 1, Example 11) (763 mg), and the reaction is stirred 6 hours at 65° C. The reaction is cooled, is diluted with 25 ml ethyl acetate, and is washed with 4×25 ml 50% saturated 1:1 sodium chloride/sodium bicarbonate. The organics are dried over anhydrous magnesium sulfate and are concentrated in vacuo to a white solid. The crude material is chromatographed over 25 g silica gel (230–400 mesh), eluting with 4% methanol/dichloromethane while collecting 5 ml fractions. Fractions 33–69 are combined and concentrated to give 256 mg of a white solid which is washed with ethyl acetate to afford 227 mg (25%) of the title compound as a white solid, mp 155–156° C, $[\alpha]^{25}_D$ −76° (c 0.30).

EXAMPLE 14

Preparation of (−)-N-[[3-[4-(4-Cyano-1H-pyrazol-1-yl)-3-fluorophenyl]-4,5-dihydro-5-isoxazolyl]methyl]acetamide

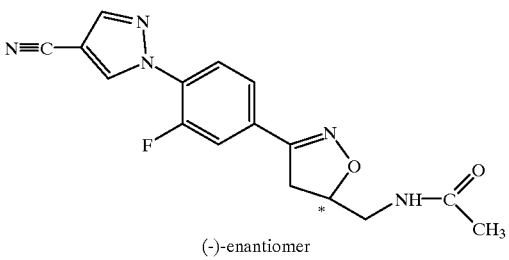

(−)-enantiomer

Step 1: (−)5-(Acetamidomethyl)-3-(3,4-difluorophenyl)-isoxazoline (Step 1, Example 11) (3.06 g) is combined with hydrazine hydrate (2.9 ml) in 6 ml t-butanol in a 48 ml screw cap pressure tube under nitrogen. The reaction is warmed to 135° C. for 6 hours, is cooled to room temperature, and is diluted with 30 ml water. The solids are collected, are washed with water, and the solid is dried. The aqueous layer is washed with 6×50 ml 10% methanol/chloroform and the combined organics are dried over anhydrous potassium carbonate. The dried organics are concentrated in vacuo to a yellow oil which is combined with the white solid. The mixture is suspended in 100 ml acetonitrile in a 200 ml one neck round bottom flask under nitrogen. The suspension is treated dropwise with acetic anhydride (1.01 ml) in 5 ml acetonitrile and the mixture is stirred 2 hours at room temperature. The solid is collected by filtration, is washed with diethyl ether, and is dried to give 950 mg of a crude white solid. Recrystallization from methanol to provide 845 mg of the hydrazine adduct with mp 212–214° C., $[\alpha]^{25}_D$ −76° (c 0.59, DMSO).

Step 2: (−)5-Acetamidomethyl-3-(3-fluoro-4-hydrazinylphenyl)-isoxazoline (400 mg) is combined with sodium-3,3-dimethoxy-propionitrile-2-formylate (273 mg) in 6 ml absolute ethanol in a 25 ml one neck round bottom flask under nitrogen. The suspension is treated with 15 drops concentrated hydrochloric acid and the reaction is stirred at 60° C. for 30 minutes. The reaction is cooled, the volatiles are removed in vacuo, and the residue is diluted with water and saturated sodium bicarbonate. The yellow solid is collected, washed with water and is dried to give a yellow solid. The crude material is chromatographed over 30 g silica gel (230–400 mesh), eluting with 5% methanol/dichloromethane while collecting 5 ml fractions. Fractions 11–30 are combined and concentrated to give 365 mg of the title compound as a pale yellow solid, mp 170–172° C. $[\alpha]^{25}_D$ −77° (c 0.67).

EXAMPLE 15

Preparation of (-)-N-[[3-[3-Fluoro-4-(3-formyl-1H-pyrrol-1-yl)phenyl]-4,5-dihydro-5-isoxazolyl]methyl]acetamide

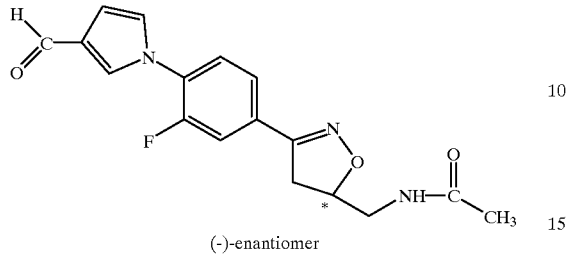

(-)-enantiomer

3-Formylpyrrole (628 mg) is dissolved in 12 ml dimethylformamide in a 50 ml one neck round bottom flask under nitrogen. The solution is cooled to 0° C., is treated with 60% sodium hydride (554 mg), and the mixture is stirred 30 minutes at room temperature. The solution is treated with (-)-5-(acetamidomethyl)-3-(3,4-difluorophenyl)-isoxazoline (Step 1, Example 11) (1.52 g), and the reaction is stirred 6 hours at 65° C. The reaction is cooled, is diluted with 100 ml ethyl acetate, and is washed with 4×25 ml 50% saturated sodium chloride. The organics are dried over anhydrous potassium carbonate and are concentrated in vacuo to a yellow oil. The crude material is chromatographed over 75 g silica gel (230–400 mesh) eluting with 3% methanol/dichloromethane and after a 200 ml forerun collecting 9 ml fractions. Fractions 48–69 are combined and concentrated to give 1.10 g (56%) of the title compound as a white solid, mp 155–156° C., $[\alpha]^{25}_D$ -69° (c 0.61, ethanol).

EXAMPLE 16

Preparation of (-)-N-[[3-[3-Fluoro-4-[3-[(hydroxyimino)methyl]-1H-pyrrol-1-yl]phenyl]-4,5-dihydro-5-isoxazolyl]methyl]acetamide

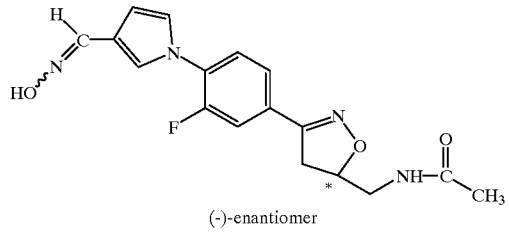

(-)-enantiomer (-)-5-Acetamidomethyl-3-(3-fluoro-4-(3-formylpyrrol-1-yl)phenyl)isoxazoline (Example 15) (329 mg) is suspended in 4 ml 95% ethanol in a 50 ml one neck round bottom flask under nitrogen. The suspension is treated with hydroxylamine (80 mg) followed by sodium hydroxide (60 mg) and 0.4 ml water. The reaction is stirred 1 hour at room temperature, the pH is adjusted to 7 with 5% hydrochloric acid, and the white solid is collected. The solid is collected, washed with water, and is dried to give 300 mg (87%) of the title compound as a white solid. The title compound is obtained via chromatography over silica gel (230–400 mesh), eluting with 5% methanol/dichloromethane, mp 216–217° C., $[\alpha]^{25}_D$ -67° (c 0.67, DMSO).

EXAMPLE 17

Preparation of (-)-N-[[3-[4-(3-Cyano-1H-pyrrol-1-yl)-3-fluorophenyl]-4,5-dihydro-5-isoxazolyl]methyl]acetamide

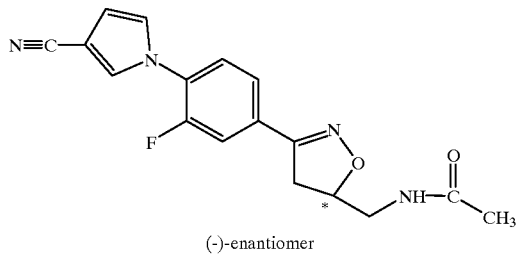

(-)-enantiomer (-)-5-Acetamidomethyl-3-(3-fluoro-4-(3-hydroximino-pyrrol-1-yl)phenyl)isoxazoline (Example 16) (486 mg) is combined with triphenylphosphine (1.48 g) and carbon tetrachloride (0.816 ml) in 14 ml acetonitrile in a 50 ml one neck round bottom flask under nitrogen. The mixture is stirred 1 hour at room temperature and the volatiles are removed in vacuo to give a pale yellow oil. The crude material is chromatographed over 35 g silica gel (230–400 mesh) eluting with 4% methanol/dichloromethane while collecting 5 ml fractions. Fractions 39–50 are combined and concentrated to give 224 mg of a white solid. The solid is washed with diethyl ether and is dried to give 160 mg of the title compound as a white solid, mp 159–161° C., $[\alpha]^{25}_D$ -72° (c 0.53, DMSO).

EXAMPLE 18

Preparation of (-)-N-[[3-[3-Fluoro-4-(1H-pyrrol-1-yl)phenyl]-4,5-dihydro-5-isoxazolyl]methyl]ethanethioamide

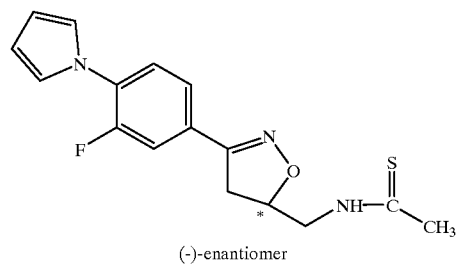

(-)-enantiomer (-)-5-Acetamidomethyl-3-(3-fluoro-4-(pyrrol-1-yl)phenyl)isoxazoline (Example 12) (452 mg) is combined with Lawesson's Reagent (655 mg) in 5 ml dioxane in a 25 ml one neck round bottom flask under nitrogen. The reaction is warmed to reflux for 30 minutes and is cooled to room temperature. The insoluble material is removed by filtration and the filtrate is concentrated in vacuo to an amber syrup. The crude material is chromatographed two times over 25 g silica gel (230–400 mesh), eluting with 3% methanol/dichloromethane while collecting 5 ml fractions. Fractions 10–30 are combined and concentrated to provide 345 mg of the title compound as an off-white solid, mp 152–153° C., $[\alpha]^{25}_D$ -27 (c 0.60, ethanol).

EXAMPLE 19

Preparation of (±)-N-[[3-[3-Fluoro-4-(3-formyl-1H-pyrrol-1-yl)phenyl]-4,5-dihydro-5-isoxazolyl]methyl]ethanethioamide

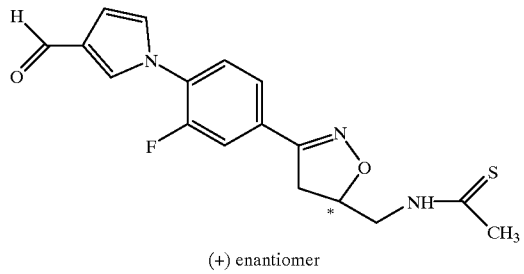

(+) enantiomer

Step 1: (−)-5-(Acetamidomethyl)-3-(3,4-difluorophenyl)-isoxazoline (Step 1, Example 11) (1.02 g) is combined with Lawesson's Reagent (1.75 g) in 20 ml doxane in a 50 ml one neck round bottom flask under nitrogen. The reaction is warmed to reflux for 30 minutes, is cooled to room temperature, and the insoluble material is removed by filtration. The filtrate is concentrated in vacuo to a pale oil which is chromatographed twice over 50 g silica gel (230–400 mesh) eluting with 25% ethyl acetate/hexane while collecting a 150 ml forerun followed by 9 ml fractions. Fractions 27–82 are combined and concentrated to provide 1.07 g (99%) of (+)-3-(3,4-difluorophenyl)-5-(thioacetamidomethyl)isoxazoline as a white solid, mp 91–92° C., $[\alpha]^{25}_D$ 46° (c 0.50, chloroform).

Step 2: 3-Formylpyrrole (314 mg) is dissolved in 6 ml dimethylformamide in a 50 ml one neck round bottom flask under nitrogen. The solution is cooled to 0° C., is treated with 60% sodium hydride (132 mg), and the mixture is stirred 30 minutes at room temperature. The solution is treated with (+)-3-(3,4-difluorophenyl)-5-(thioacetamidomethyl)isoxazoline (810 mg), and the reaction is stirred 6 hours at 65° C. The reaction is cooled, is diluted with 50 ml ethyl acetate, and is washed with 4×25 ml 50% saturated 1:1 sodium chloride/sodium bicarbonate. The organics are dried over anhydrous potassium carbonate and are concentrated in vacuo to an amber oil. The crude material is chromatographed over 50 g silica gel (230–400 mesh) eluting with 30% ethyl acetate/hexane and after a 200 ml forerun collecting 9 ml fractions. Fractions 48–63 are combined and concentrated to give 202 mg of the title compound as solid, mp 149–150° C., $[\alpha]^{25}_D$ 68° (c 0.52, chloroform).

EXAMPLE 20

Preparation of (−)-N-[[3-[3-Fluoro-4-[3-(hydroxymethyl)-1H-pyrrol-1-yl]phenyl]-4,5-dihydro-5-isoxazolyl]methyl]acetamide

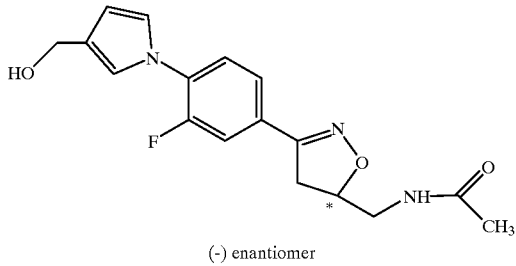

(-) enantiomer (−)-5-Acetamidomethyl-3-(3-fluoro-4-(3-formyl-pyrrol-1-yl)phenyl)isoxazoline (Example 15) (658 mg) is suspended/dissolved in 20 ml methanol under nitrogen. The mixture is treated with sodium borohydride (76 mg) and the reaction is stirred 1 hour at room temperature. The reaction is diluted with 1×10 ml 2N sodium hydroxide and the volatiles are removed in vacuo. The residue is diluted with 20 ml water and the white solid is collected and dried to give 609 mg of the title compound as an off white solid, mp 162–164° C., $[\alpha]^{25}_D$ −72° (c 0.54, methanol).

EXAMPLE 21

Preparation of (−)-N-[[3-[4-(4-Acetyl-1-piperazinyl)-3-fluorophenyl]-4,5-dihydro-5-isoxazolyl]methyl]acetamide

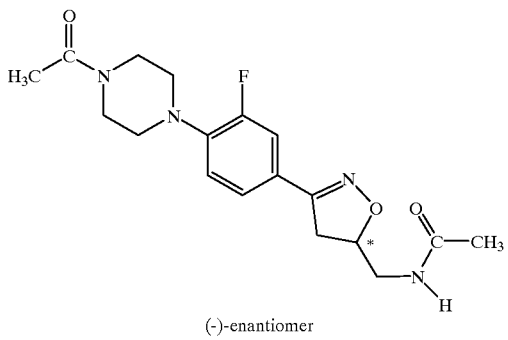

(-)-enantiomer

Step 1: A resealable tube containing (−)-N-[[4,5-dihydro-3-(4-fluorophenyl)-5-isoxazolyl]methyl]acetamide (Step 1, Example 11) (600 mg) and piperazine (2.03 g) is heated to approximately 120° C. for 20 hours. The reaction vessel is cooled to room temperature, the mixture diluted with $CH_2Cl_2$ and water and then transferred to a separator funnel. The aqueous phase is salted and some 5% aqueous MeOH added. The aqueous phase is extracted with $CH_2Cl_2$ (3×50 mL). The combined organic phases are dried over sodium sulfate, concentrated in vacuo to give a tan solid. Chromatography over silica gel, eluting with 95:5 $CHCl_3$/MeOH, 1% NH₄OH afforded, after combination of appropriate fractions and concentration in vacuo, 0.532 g (70%) of the piperazine adduct as a solid, mp 159–163° C.

Step 2: To a flask containing (−)-N-[[4,5-dihydro-3-[3-fluoro-4-(1-piperazinyl)phenyl]-5-isoxazolyl]methyl]acetamide (110 mg) in methylene chloride (10 mL) and triethylamine (0.09 mL) is added acetyl chloride (0.03 mL) at 0° C. under an inert atmosphere. The reaction is warmed to ambient temperature, stirred fifteen hours, concentrated in vacuo, and chromatographed on silica gel (230–400 mesh, 100 mL), eluting with chloroform/methanol (95/5). The appropriate fractions are combined (R$_f$=0.14, TLC, chloroform/methanol, 95/5) and concentrated in vacuo to give the title compound, mp 248–250° C., [α]$^{25}_D$ −60°.

EXAMPLE 22

Preparation of (−)-N-[[3-[4-[4-[(2,3-Dihydro-1,4-benzodioxin-2-yl)carbonyl]-1-piperazinyl]-3-fluoropheny]-4,5-dihydro-5-isoxazolyl]methyl]acetamide

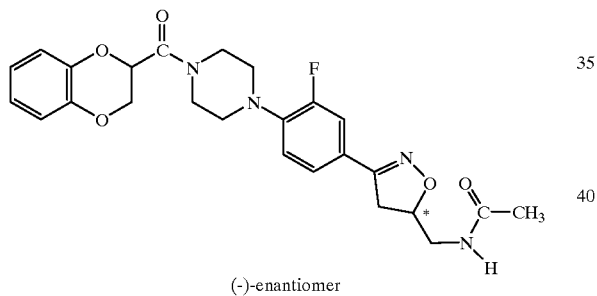

(−)-enantiomer

To a flame dried flask containing (−)-N-[[4,5-dihydro-3-[3-fluoro-4-(1-piperazinyl)phenyl]-5-isoxazolyl]methyl]acetamide (Step 1, Example 21) (200 mg), 1,4-benzodioxan-2-carboxylic acid (135 mg), DMAP (9 mg) in pyridine (7 mL) is added EDC (144 mg) at ambient temperature and stirred for 48 hours. The reaction is diluted with CH₂Cl₂ (25 mL) and washed with H₂0 (2×50 mL) and saline (50 mL). The organic phase is dried over sodium sulfate, concentrated in vacuo and chromatographed on silica gel (230–400 mesh), eluting with chloroform/methanol (99/1). The appropriate fractions are combined (R$_f$=0.29,TLC, chloroform/methanol, 95/5), concentrated to give the title compound, mp 158–161° C., [α]$^{25}_D$ −430 (CHCl₃).

EXAMPLE 23

Preparation of (−)-N-[[3-[3-Fluoro-4-[4-(hydroxyacetyl)-1-piperazinyl]phenyl]-4,5-dihydro-5-isoxazolyl]methyl]acetamide

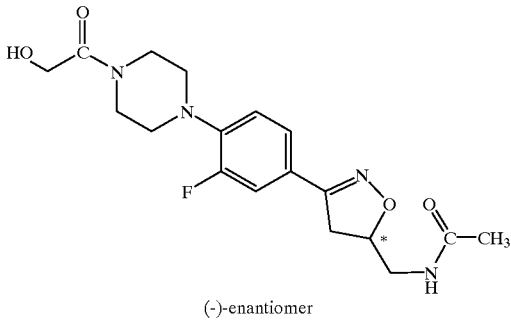

(−)-enantiomer

The final product of Example 2 is chromatographed with a preparative Chiralpak AD column, eluting with iospropanol/heptane, to separate the individual enantiomers. The (−)-enantiomer so obtained is further purified by column chromatography over silica gel, eluting with a gradient of 1–5% CH₂Cl₂/MeOH, to give, after combination of appropriate fractions and concentration in vacuo, the title compound as a white solid, mp 228–229° C., [α]$^{25}_D$ −59° (c 0.96, DMSO).

EXAMPLE 24

Preparation of (−)-N-[[3-[3-Fluoro-4-(4-morpholinyl)phenyl]-4,5-dihydro-5-isoxazolyl]methyl]acetamide

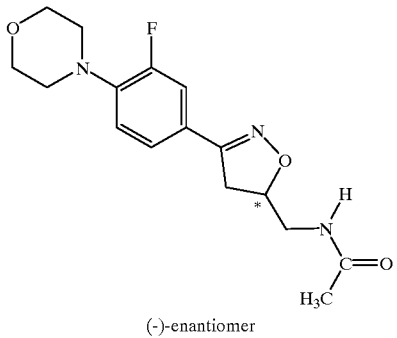

(−)-enantiomer

To a resealable tube containing (+/−)-N-[[4,5-dihydro-3-(3,4-difluorophenyl)-5-isoxazolyl]methyl]acetamide (Step 3, Example 3) (1.70 g) in morpholine (5.83 mL) is added potassium carbonate (1.16 g) and heated to 140° C. for 48 hours. The reaction is diluted with CH₂Cl₂ (50 mL) and washed with H₂O (3×50 mL) and saline (50 mL). The organic phase is dried over sodium sulfate, concentrated in vacuo and chromatographed on silica gel (230–400 mesh), eluting with methylene chloride/methanol (98.5/1.5). The appropriate fractions are combined (R_f=0.30, TLC, chloroform/methanol, 95/5) and concentrated in vacuo to give the title compound. The racemic material is separated on chiral HPLC (Chiralpak AD column, eluting with 8:2:1.5 heptane/isopropanol/chloroform) to give the individual enantiomers, the title compound having mp 179–180° C., $[\alpha]^{25}_D$ –71° (DMSO).

EXAMPLE 25

Preparation of (–)-N-[[3-[3,5-Difluoro-4-(1-piperazinyl)phenyl]-4,5-dihydro-5-isoxazolyl]methyl]acetamide

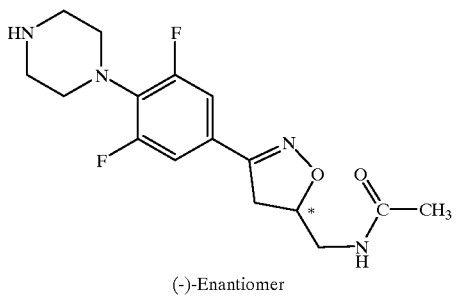

(–)-Enantiomer

Racemic 5-(Acetamidomethyl)-3-(3,4,5-trifluorophenyl) isoxazoline (Step 3, Example 9) is chromatographed on a preparative Chiralpak AD column, eluting with isopropanol/heptane, to provide the separated enantiomers. The (–)-5-(acetamidomethyl)-3-(3,4,5-trifluorophenyl)isoxazoline is converted to the title compound by reacting it with piperazine, as described previously for racemic material (Step 4, Example 9). The title compound is obtained as a white solid (45% yield), mp 149–151° C., $[\alpha]^{25}_D$ –67° (c 0.79, DMSO).

EXAMPLE 26

Preparation of (–)-N-[[3-[4-[4-[(2,3-Dihydro-1,4-benzodioxin-2-yl)carbonyl]-1-piperazinyl]-3,5-difluorophenyl]-4,5-dihydro-5-isoxazolyl]methyl]acetamide

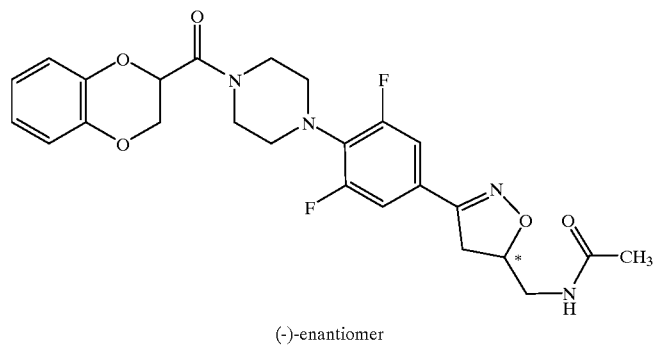

(–)-enantiomer

To a flame dried flask containing (–)-N-[[4,5-dihydro-3-[3,5-difluoro-4-(1-piperazinyl)phenyl]-5-isoxazolyl]methyl]acetamide (see Example 25) (175 mg), 1,4-benzodioxan-2-carboxylic acid (112 mg, 0.0.62 mmol), DMAP (7 mg) in pyridine (~5 mL) is added EDC (119 mg) at ambient temperature and stirred for 3 days. The reaction is diluted with CH$_2$Cl$_2$ (25 mL) and washed with H$_2$O (2×50 mL) and saline (50 mL). The organic phase is dried over sodium sulfate, filtered and concentrated in vacuo and chromatographed on silica gel (230–400 mesh, 100 mL), eluting with chloroform/methanol. The appropriate fractions are combined and concentrated to give the title compound, mp 158–159° C., $[\alpha]^{25}_D$ –41° (CHCl$_3$).

EXAMPLE 27

Preparation of (–)-N-[[3-[3,5-Difluoro-4-[4-(hydroxyacetyl)-1-piperazinyl]phenyl]-4,5-dihydro-5-isoxazolyl]methyl]acetamide

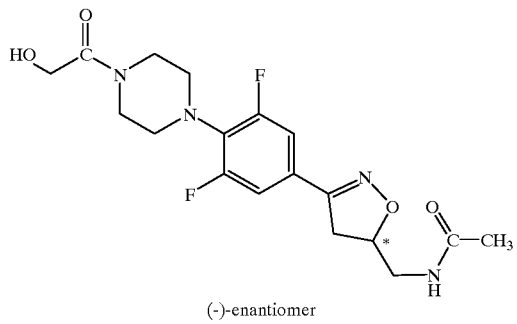

(–)-enantiomer

Following the procedure of Example 23, but starting with the final product of Example 25 (250 mg), 195 mg (67%) of the title compound is obtained as a white solid, mp 220–221° C, $[\alpha]^2_D$ –60° (c 0.94, DMSO).

EXAMPLE 28

Preparation of (−)-N-[[3-[3,5-Difluoro-4-(1H-imidazol-1-yl)phenyl]-4,5-dihydro-5-isoxazolyl]methyl]acetamide

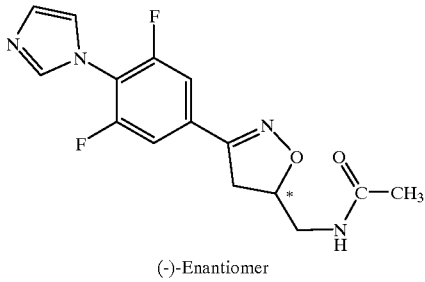

(−)-Enantiomer

A solution of imidazole (42 mg) in dry DMF (5 mL) is treated with 60% sodium hydride dispersion in mineral oil (25 mg), stirred for 3 minutes and treated with (−)-5-(acetamidomethyl)-3-(3,4,5-trifluorophenyl)isoxazoline (see Example 25) (150 mg). After 18 hours, the mixture is heated to 40° C. for 2 hours. TLC analysis (5% CH₃OH—CH₂Cl₂) indicated the reaction to be virtually complete. The mixture is diluted with water (50 mL) and extracted with EtOAc (6×20 mL), dried over Na₂SO₄, filtered and concentrated under reduced pressure to give a white solid. Chromatography over silica (radial chromatography, 2 mm plate) eluting with CH₂Cl₂, 2% and 5% CH₃OH—CH₂Cl₂ gives 100 mg of the title compound as a white solid, mp 168–169° C., $[\alpha]^{25}_D$ −80° (c 0.61, DMSO).

EXAMPLE 29

Preparation of N-[[3-[3,5-Difluoro-4-(1H-imidazol-1-yl)phenyl]-4,5-dihydro-5-isoxazolyl]methyl]ethanethioamide

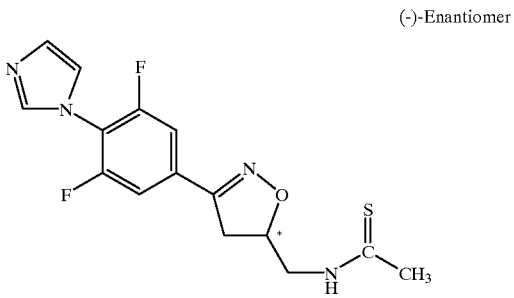

(−)-Enantiomer

A mixture of the final product of Example 28 (150 mg) and [2,4-bis(4-methoxyphenyl)-1,3-dithia-2,4-diphosphetane-2,4-disulfide (Lawesson's Reagent) (189 mg) in 1,4-dioxane (5 mL) is heated at reflux for 1.5 hours and stirred at ambient temperature. After 18 hours, TLC analysis (5% CH₃OH—CH₂Cl₂) indicated the reaction to be complete. The mixture is diluted with water (50 mL), extracted with EtOAc (3×25 mL), dried over Na₂SO₄, filtered and concentrated under reduced pressure to a light yellow solid. The crude material is recrystallized from 5%CH₃OH/EtOAc to give 119 mg of the title compound as a white solid, mp 238–240° C. dec and MS(ES) 337 (M+H)⁺ $[\alpha]^{25}_D$.

EXAMPLE 30

Preparation of (−)-N-[[3-[3,5-Difluoro-4-(4-morpholinyl)phenyl]-4,5-dihydro-5-isoxazolyl]methyl]ethanethioamide

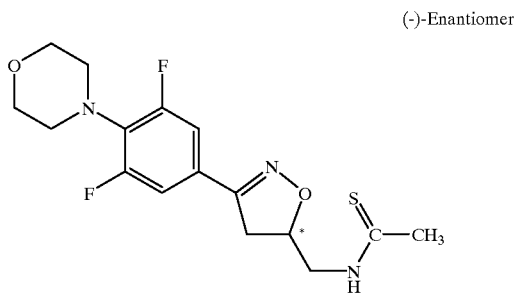

(−)-Enantiomer

Following the procedure of Example 29, a sample of Example 31 (150 mg, 0.44 mmol) is converted to the title compound, which is obtained as a white solid (97% yield), mp 194–195° C., $[\alpha]^{25}_D$ −39° (c 0.98, DMSO).

EXAMPLE 31

Preparation of (−)-N-[[3-[3,5-Difluoro-4-(4-morpholinyl)phenyl]-4,5-dihydro-5-isoxazolyl]methyl]acetamide

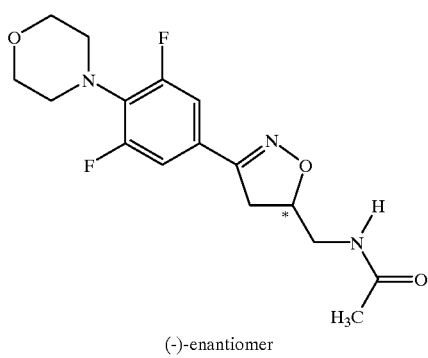

(−)-enantiomer

Example 10 (racemic mixture) is subjected to preparative chiral HPLC conditions (Chiralpak AD column, eluting with isopropanol/heptane) to separate the enantiomers. (−)-N-[[4,5-Dihydro-3-[3,5-difluoro-4-(4-morpholino)phenyl]-5-isoxazolyl]methyl]] is obtained as a white solid, mp 153–155° C., $[\alpha]^{25}_D$ −65°.

EXAMPLE 32

Preparation of N-({3-[3-fluoro-4-(4-thiomorpholinyl)phenyl]-4,5-dihydro-5-isoxazolyl{methyl)acetamide

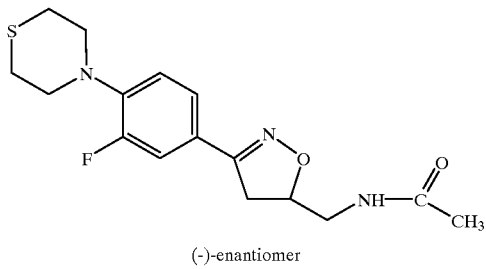

(−)-enantiomer

Following the general procedure of EXAMPLE 3, and making non-critical variations but using (−) enantiomer of 5-Acetamidomethyl-3-(3,4-difluorophenyl)isoxazoline as the displacement substrate with 4-thiomorpholine, the title compound is obtained as a solid. mp=188–189° C.

EXAMPLE 33

Preparation of N-({3-[3-fluoro-4-(1-oxo-1lambda⁴,4-thiazinan-4-yl)phenyl}-4,5-dihydro-5-isoxazolyl}methyl)acetamide

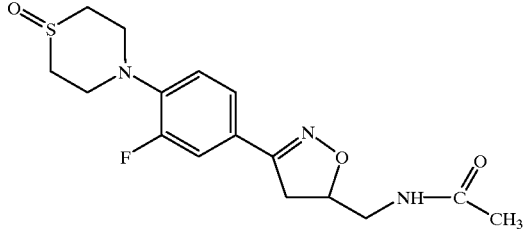

1.0 g (2.97 mmol) of N-({3-[3-fluoro-4-(4-thiomorpholinyl)phenyl]-4,5-dihydro-5-isoxazolyl}methyl) acetamide is suspended in 20 ml methanol/5 ml acetone in a 100 ml one neck round bottom flask. The suspension is treated with sodium meta periodate (666 mg, 3.12 mmole) in 20 ml water and the reaction mixture is stirred 48 hours at room temperature. The organics are removed in vacuo and the aqueous residue is filtered to remove a fine white solid. The solid is washed with water followed by diethyl ether to give 902 mg the title compound) as a solid. mp=204–205° C.

EXAMPLE 34

Preparation of N-({3-[3-fluoro-4-(4-thiomorpholinyl)phenyl]-4,5-dihydro-5-isoxazolyl}methyl)ethanethioamide

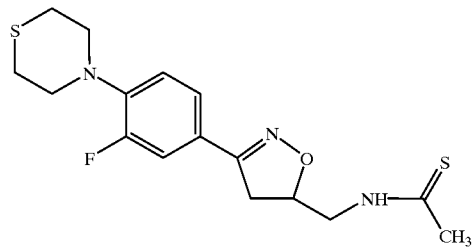

1.0 g (3.0 mmole) of N-({3-[3-fluoro-4-(4-thiomorpholinyl)phenyl]-4,5-dihydro-5-isoxazolyl}methyl) acetamide is suspended in 12 ml dioxane in a 50 ml one neck round bottom flask under nitrogen. The suspension is treated with Lawesson's Reagent (1.27 g, 3.15 mmole) and the reaction is stirred at 80° C. for 1 hour. The mixture is cooled to room temperature, brought to homogeneity with dichloromethane and is treated with 10 g silica gel (230–400 mesh) and is concentrated to dryness. The plug is loaded onto a SIM and the material is chromatographed twice over 40 g silica gel (BIOTAGE), eluting with 7% acetone/dichloromethane while collecting 25 ml fractions. Fractions 6–13 are combined and concentrated to afford 902 mg (85%) of the title compound as a solid. mp=219–220° C.

EXAMPLE 35

Preparation of N-({3-[3-fluoro-4-(1-oxo-1lambda⁴,4-thiazinan-4-yl)phenyl}-4,5-dihydro-5-isoxazolyl}methyl)ethanethioamide

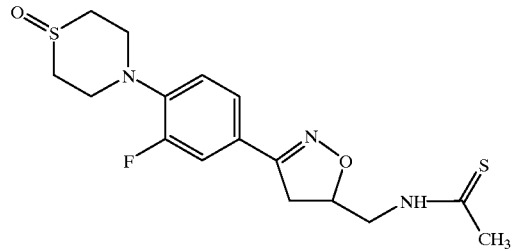

423 mg (1.0 mmole) of N-({3-[3-fluoro-4-(1-oxo-1lambda⁴,4-thiazinan-4 -yl)phenyl}-4,5-dihydro-5-isoxazolyl}methyl)acetamide is combined with 1.5 ml hydrazine hydrate and 1.5 ml dimethylsulfoxide in a 15 ml screw cap pressure tube. The reaction is heated to 130° C. for 24 hours. The mixture is cooled to room temperature, is diluted with 25 ml 50% saturated sodium chloride, and is extracted with 5×20 ml 5% methanol/chloroform. The organics are dried over potassium carbonate and are concentrated in vacuo to give 325 mg (87%) of N-({3-[3-fluoro-4-(1-oxo-1lambda⁴,4-thiazinan-4-yl)phenyl}-4,5-dihydro-5-isoxazolyl}methyl)amine. The crude solid, 315 mg (1.01 mmole) is dissolved in 10 ml 1:1 dichloromethane/tetrahydrofuran in an oven dried 50 ml two neck round bottom flask under nitrogen. The solution is treated with triethylamine (0.28 ml, 2.02 mmole) followed by ethyl dithioacetate (0.23 ml, 2.02 mmole) and the reaction is stirred 1 hour at room temperature. The suspension is brought to homogeneity with chloroform, is treated with 4 g silica gel (230–400 mesh), and is concentrated to dryness. The plug is chromatographed over 30 g silica gel (230–400 mesh) eluting with 2% methanol/dichloromethane for a 350 ml forerun followed by 3% methanol/dichloromethane while collecting 50 ml fractions. Fractions 2–5 are combined and concentrated to provide 277 mg (75%) of the title compouns as solid. mP=199° C.

We claim:

1. A compound of the formula I

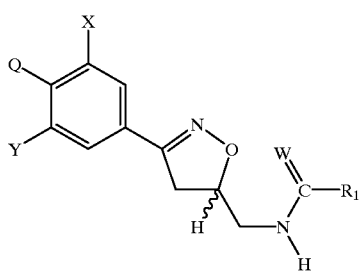

I or pharmaceutically acceptable salts thereof wherein:

$R_1$ is
(a) H,
(b) $C_{1-8}$ alkyl, which may be substituted with one or more halo, —OH, $C_{1-4}$ alkoxy or $C_{1-4}$ acyloxy,
(c) $C_{3-6}$ cycloalkyl,
(d) $C_{1-8}$ alkoxy,
(e) amino, or
(f) NH($C_{1-3}$ alkyl), wherein $C_{1-3}$ alkyl may be substituted with one or more halo;

X and Y are independently
(a) H,
(b) F, or
(c) $CH_3$;

W is
(a) O, or
(b) S;

Q is
(a) a 5-membered heterocyclic moiety having one to four nitrogen atoms selected from structures consisting of i, ii, iii, iv, v, vi, vii, viii, and ix;

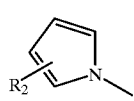

i

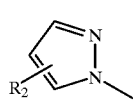

ii

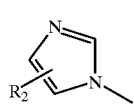

iii

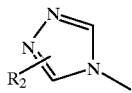

iv

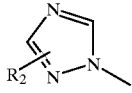

v

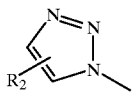

vi

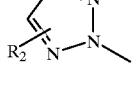

vii

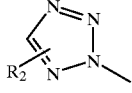

viii

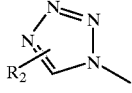

ix (b) a 9-membered heterocyclic moiety having one to four nitrogen atoms selected from structures consisting of x, xi, xii, xiii, xiv, xv, xvi, xvii, and xviii;

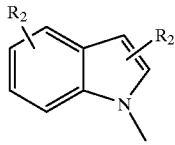

x

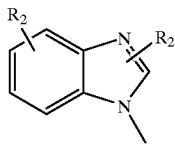

xi

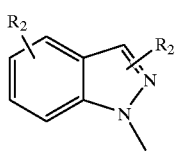

xii xiii

-continued

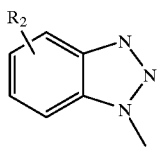
xiv

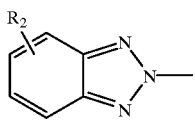
xv

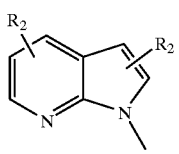
xvi

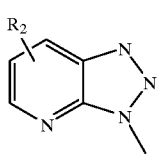
xvii

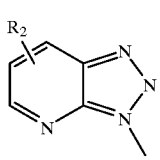
xviii (c) a heterocyclic ring having a nitrogen atom selected from structures consisting of xix, xx, xxi, xxii, and xxiii;

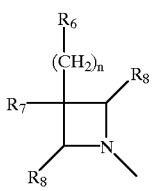
xix

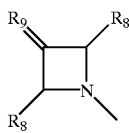
xx

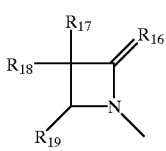
xxi

-continued

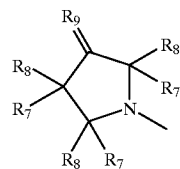
xxii

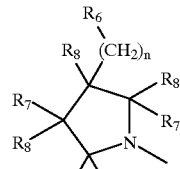
xxiii

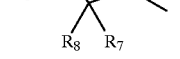
(d)

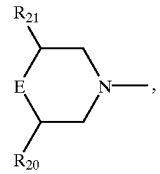
(e)

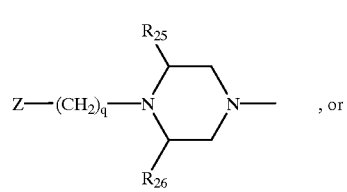
, or (f)

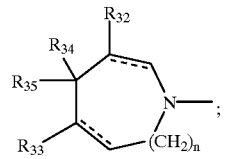

wherein $R_2$ is
(a) H,
(b) halo,
(c) —OH,
(d) —OR$_3$,
(e) —SR$_3$,
(f) —S(O)$_r$R$_3$,
(g) —CN,
(h) —O$_2$CR$_3$,
(i) —NHC(=O)R$_3$,
(j) —NHCO$_2$R$_3$,
(k) —NHSO$_2$R$_3$,
(l) —CO$_2$R$_4$,
(m) —C(=O)N(R$_3$)$_2$,
(n) —C(=O)R$_3$,
(o) $C_{1-8}$ alkyl,
(p) $C_{3-8}$ cycloalkyl,
wherein groups (o) and (p) may be substituted with one or more of the preceding groups (a)–(n),
(q) phenyl, which may be substituted with one or more of the preceding groups (a)–(p),
(r) —CH=CHCO$_2$Et, or
(s) —C(=NR$_4$)R$_5$;

$R_3$ is
- (a) H,
- (b) $C_{1-6}$ alkyl,
- (c) $C_{3-8}$ cycloalkyl, wherein groups (b) and (c) may be substituted with one or more of halo, —OH, $C_{1-4}$ alkoxy, $C_{1-4}$ acyl, $C_{1-4}$ acyloxy, or —OC(=O)CH$_2$N(CH$_3$)$_2$, or
- (d) phenyl, which may be substituted with one or more of the preceding groups (b) to (c);

$R_4$ is
- (a) —OH or
- (b) —OCH$_3$;

$R_5$ is
- (a) H, or
- (b) —CH$_3$;

wherein $R_6$ is
- (a) H,
- (b) —OR$_{10}$,
- (c) —SR$_{10}$,
- (d) —NR$_{11}$R$_{12}$,
- (e) —CN,
- (f) $C_{1-4}$ alkoxycarbonyl,
- (g) carboxamide,
- (h) $C_{1-4}$ acyl, which may be substituted with one or more halo, —OH, $C_{1-4}$ alkoxy or $C_{1-4}$ acyloxy,
- (i) —N(OH)($C_{1-6}$ alkyl),
- (j) —N(OH)CH$_2$ phenyl,
- (k) —NSO$_2$($C_{1-6}$ alkyl) wherein $C_{1-6}$ alkyl may be substituted with one or more halo, $C_{1-6}$ alkoxy or phenyl, or
- (l) F;

$R_7$ is
- (a) H,
- (b) —OH,
- (c) —O($C_{1-6}$ alkyl),
- (d) $C_{1-4}$ alkyl,
- (e) phenyl, or
- (f) F;

$R_8$ is
- (a) H,
- (b) $C_{1-3}$ alkyl, which may be substituted with halo, —OH, —CO$_2$ $C_{1-4}$ alkyl, $C_{1-3}$ acyloxy, $C_{1-3}$ alkyoxy or —N($C_{1-4}$ alkyl)$_2$,
- (c) phenyl, or
- (d) pyridyl;

$R_9$ is
- (a) O,
- (b) S,
- (c) —NR$_{13}$, or
- (d) —CR$_{14}$R$_{15}$;

$R_{10}$ is
- (a) H,
- (b) $C_{1-8}$ alkyl, which may be substituted with one or more halo, —CN, —OH, $C_{1-8}$ alkoxy, $C_{1-8}$ acyloxy, $C_{1-4}$ alkoxycarbonyl, or phenyl,
- (c) $C_{1-8}$ acyl, which may be substituted with one or more —OH, $C_{1-8}$ alkoxy, $C_{1-8}$ acyloxy,
- (d) $C_{1-8}$ alkoxycarbonyl,
- (e) carboxamide, which may be substituted with a $C_{1-4}$ alkyl or phenyl on the carboxamide nitrogen, or
- (f) phenyl, which may be substituted with one or more halo, —CN, $C_{1-3}$ alkoxy, $C_{1-3}$ alkoxycarbonyl or $C_{1-4}$ alkyl;

$R_{11}$ and $R_{12}$ are independently
- (a) H,
- (b) $C_{1-8}$ alkyl, which may be substituted with one or more halo, —CN, —OH, $C_{1-8}$ alkoxy, $C_{1-8}$ acyloxy, $C_{1-8}$ alkoxycarbonyl, phenyl,
- (c) $C_{1-8}$ acyl, which may be substituted with one or more —OH, amino, $C_{1-8}$ alkoxy, $C_{1-8}$ acyloxy, $C_{1-4}$ acylamino,
- (d) benzoyl, which may be substituted with one or more halo, —OH, amino, $C_{1-8}$ alkoxy, $C_{1-8}$ acyloxy, $C_{1-4}$ acylamino, $C_{1-4}$ alkoxycarbonylamino,
- (e) $C_{1-8}$ alkoxycarbonyl,
- (f) benzyloxycarbonyl,
- (g) tertbutoxycarbonyl,
- (h) carboxamide, which may be substituted with a $C_{1-4}$ alkyl or phenyl on the carboxamide nitrogen,
- (i) trifluoracetyl, or
- (j) $C_{1-6}$ acyl;

$R_{13}$ is
- (a) H,
- (b) —OR$_{10}$,
- (c) —NHR$_{10}$, or
- (d) $C_{1-8}$ alkyl, which may be substituted with phenyl;

$R_{14}$ and $R_{15}$ are independently
- (a) H,
- (b) $C_{1-4}$ alkyl, which may be substituted with halo, —OH, $C_{1-4}$ alkoxy, $C_{1-4}$ alkoxycarbonyl, or phenyl,
- (c) $C_{1-8}$ acyl,
- (d) $C_{1-4}$ alkoxycarbonyl,
- (e) —CN, or
- (f) F;

$R_{16}$ is
- (a) O, or
- (b) S;

$R_{17}$ and $R_{18}$ are independently
- (a) H,
- (b) $C_{1-4}$ alkyl, which may be substituted with halo, —OH or $C_{1-4}$ alkoxy,
- (c) —OH,
- (d) $C_{1-4}$ alkoxy, which may be substituted with —OH or $C_{1-4}$ alkoxy,
- (e) NR$_{11}$R$_{12}$, or
- (f) $C_{1-4}$ acyloxy;

$R_{19}$ is
- (a) H, or
- (b) —CH$_3$;

E is
- (a) —O—, or
- (b) —S(=O)$_m$—;

$R_{20}$ is
- (a) H,
- (b) —CH$_3$,
- (c) —CN,
- (d) —CO$_2$H,
- (e) —CO$_2$R$_{22}$, or
- (f) —(CH$_2$)$_i$R$_{23}$;

$R_{21}$ is
- (a) H, or
- (b) —CH$_3$;

$R_{22}$ is
- (a) H,
- (b) $C_{1-6}$ alkyl, which may be substituted with halo, —OH, $C_{1-4}$ alkoxy, $C_{1-4}$ acyloxy or —O—CH$_2$-phenyl,
- (c) $C_{3-6}$ cycloalkyl,
- (d) amino,
- (e) —N($C_{1-6}$ alkyl)$_2$,
- (f) —NH($C_{1-6}$ alkyl), or
- (g) $C_{1-6}$ alkoxy;

$R_{23}$ is
- (a) —OH,
- (b) —OR$_{22}$,
- (c) —OC(=O)R$_{22}$,
- (d) amino,
- (e) —NHC(=O)R$_{22}$, or
- (f) —N(R$_{24}$)$_2$;

$R_{24}$ is
- (a) H,
- (b) C$_{1-4}$ alkyl, which may be substituted with halo, —OH, C$_{1-4}$ alkoxy, amino, —N(C$_{1-6}$ alkyl)$_2$, or —NH(C$_{1-6}$ alkyl), or
- (c) p-toluenesulfonyl;

wherein Z is
- (a) H,
- (b) —C(=O)R$_{27}$,
- (c) C$_{1-6}$ alkyl,
- (d) benzyl,
- (e) phenyl, wherein groups (d) and (e) may be substituted with one or more halo, —OCH$_3$, —OH, amino or C$_{1-4}$ alkyl,
- (f) —OR$_{28}$,
- (g) —OC(=O)R$_{29}$,
- (h) —S—C$_{1-6}$ alkyl,
- (i) —SO$_2$—C$_{1-6}$ alkyl,
- (j) phenylsulfonyl,
- (k) p-toluenesulfonyl,
- (l) —SO$_2$—N(R$_{30}$)$_2$,
- (m) —C(O)—OR$_{31}$,
- (n) —C(O)—N(R$_{30}$)$_2$,
- (o) —N(R$_{30}$)$_2$, or
- (p) a 6-membered heterocyclic moiety having one to three nitrogen atoms selected from structures consisting of xxiv, xxv, xxvi, xxvii, xxviii, xxix,

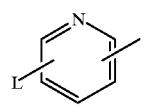

xxiv

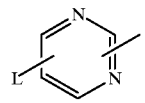

xxv

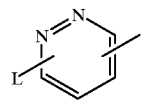

xxvi

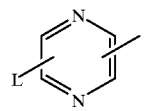

xxvii

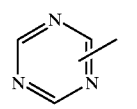

xxviii

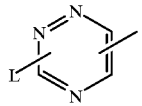

xxix

L is
- (a) H,
- (b) amino,
- (c) C$_{1-4}$ alkyl, or
- (d) halo;

$R_{25}$ and $R_{26}$ are independently
- (a) H,
- (b) C$_{1-6}$ alkyl, or
- (c) C$_{3-6}$ cycloalkyl;

$R_{27}$ is
- (a) C$_{1-6}$ alkyl,
- (b) C$_{1-8}$ alkylhydroxyl,
- (c) phenyl, or
- (d)

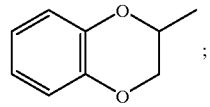

;

$R_{28}$ is
- (a) H,
- (b) C$_{1-6}$ alkyl,
- (c) vinyl, or
- (d) phenyl, which may be substituted with one to more halo, C$_{1-4}$ alkoxy, —OH, amino or C$_{1-4}$ alkyl, $R_{29}$ is
- (a) C$_{1-6}$ alkyl, or
- (b) phenyl;

$R_{30}$ is independently
- (a) H,
- (b) C$_{1-4}$ alkyl, or
- (c) phenyl, which may be substituted with C$_{1-4}$ alkyl or C$_{1-4}$ alkoxy, $R_{31}$ is
- (a) C$_{1-6}$ alkyl,
- (b) phenyl, which may be substituted with C$_{1-4}$ alkyl or C$_{1-4}$ alkoxy, or
- (c) benzyl, which may be substituted with C$_{1-4}$ alkyl or C$_{1-4}$ alkoxy;

wherein $R_{32}$ and $R_{33}$ are independently
- (a) H,
- (b) halo,
- (c) C$_{1-8}$ alkyl, which may be substituted with one or more R$_{45}$,
- (d) C$_{3-6}$ cycloalkyl,
- (e) —(CH$_2$)$_m$—OR$_{36}$, or
- (f) —C(=O)—R$_{38}$;

$R_{34}$ and $R_{35}$ are independently
- (a) H,
- (b) C$_{1-8}$ alkyl, which may be substituted with one or more R$_{45}$,
- (c) C$_{1-8}$ alkoxy,
- (d) C$_{1-8}$ alkylthio,
- (e) —(CH$_2$)$_m$—OR$_{39}$,
- (f) —O—(CH$_2$)$_m$—OR$_{39}$,
- (g) —NR$_{40}$R$_{41}$, (h) —N=CH—NR$_{42}$R$_{43}$,
(i) —C(=O)-NR$_{40}$R$_{41}$, or
(j) —(CH$_2$)$_m$—C(=A)—R$_{38}$, wherein A is O or ethyleneketal, or R$_{34}$ and R$_{35}$ together to form
(k) =O,
(l) =NR$_{44}$,
(m) =S, or
(n) =CR$_{42}$R$_{43}$;

R$_{36}$ and R$_{37}$ are independently
(a) H,
(b) C$_{1-8}$ alkyl, which may be substituted with one or more R$_{45}$, or
(c) —CH$_2$OCH$_3$;

R$_{38}$ is
(a) H,
(b) —(CH$_2$)$_m$—OH,
(c) C$_{1-8}$ alkyl, which may be substituted with one or more R$_{45}$,
(d) C$_{1-8}$ alkoxy,
(e) —O—CH$_2$—O—C(=O)—R$_{36}$, or
(f) —(CH$_2$)$_m$—C(=O)—OR$_{36}$;

R$_{39}$ is
(a) H,
(b) C$_{1-8}$ alkyl, which may be substituted with one or more R$_{45}$,
(c) C$_{2-8}$ alkenyl,
(d) —(CH$_2$)$_m$—OR$_{36}$,
(e) —(CH$_2$)$_m$—C(=O)—R$_{38}$,
(f) —C(=O)—(CH$_2$)$_m$—OR$_{43}$, or
(g) tosyl;

R$_{40}$ and R$_{41}$ are independently
(a) H,
(b) —(CH$_2$)$_m$—OR$_{36}$,
(c) C$_{1-8}$ alkyl, which may be substituted with one or more R$_{45}$,
(d) —C(=O)—R$_{38}$,
(e) —C(=O)—NR$_{36}$R$_{37}$,
(f) —(CH$_2$)$_p$-phenyl,
(g) thiazol-2-yl, or R$_{40}$ and R$_{41}$ together to form
(h) pyrrolidino,
(i) piperidino,
(j) piperazino,
(k) morpholino, or
(l) thiomorpholino, wherein groups (h) to (l) may be substituted with C$_{1-8}$ alkyl or —(CH$_2$)$_m$—OH;

R$_{42}$ and R$_{43}$ are independently
(a) H,
(b) C$_{1-8}$ alkyl, which may be substituted with one or more R$_{45}$,
(c) —C(=O)—R$_{38}$, or
(d) —(CH$_2$)$_p$-phenyl;

R$_{44}$ is
(a) H,
(b) —OR$_{39}$,
(c) C$_{1-8}$ alkyl, which may be substituted with one or more R$_{45}$,
(d) C$_{1-8}$ alkoxy,
(e) —(CH$_2$)$_p$-phenyl,
(f) —NR$_4$OR$_{41}$,
(g) —NH—C(=NH)—NH$_2$,
(h) [1,2,4]triazol-4-yl, or
(i) —CN;

R$_{45}$ is
(a) halo,
(b) —OH,
(c) —CN,
(d) C$_{1-6}$ alkoxy,
(e) amino,
(f) —N(C$_{1-6}$ alkyl)$_2$,
(g) —NH(C$_{1-6}$ alkyl), or
(h) carboxyl;

=== is a double bond or a single bond;

i is 1 or 2;

m is 0, 1 or 2;

n is 0 or 1;

p is 1, 2, 3 or 4; and q is 0, 1, 2, 3 or 4.

2. A compound of formula I according to claim 1 wherein R$_1$ is
(a) C$_{1-3}$ alkyl,
(b) C$_{1-3}$ alkoxy, or
(c) —NH(C$_{1-3}$ alkyl).

3. A compound of formula I according to claim 1 wherein R$_1$ is CH$_3$.

4. A compound of formula I according to claim 1 wherein X and Y are independently H, or F.

5. A compound of formula I according to claim 1 wherein X is H; and Y is F.

6. A compound of formula I according to claim 1 wherein W is O, or S.

7. A compound of formula I according to claim 1 wherein Q is a 5-membered heterocyclic moiety having one to four nitrogen atoms selected from structures consisting of i, ii, iii, and vi

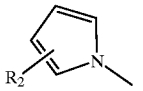 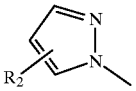 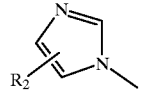
i     ii     iii

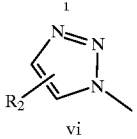
vi wherein R$_2$ is as defined in claim 1.

8. A compound of formula I according to claim 7 wherein R$_2$ is
(a) H,
(b) —CN,
(c) —C(=O)H,
(d) —C(=NH)—OH, or
(e) C$_{1-3}$ alkyl hydroxyl.

9. A compound of formula I according to claim 1 wherein Q is

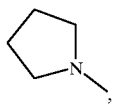
(a)

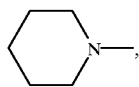 (b)

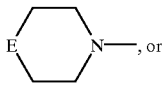 (c)

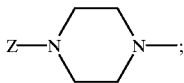 (d)

wherein E and Z are as defined in claim 1.

10. A compound of formula I according to claim 9 wherein E is —S(=O)$_m$—, and m is 0, 1 or 2.

11. A compound of formula I according to claim 9 wherein Z is
   (a) H,
   (b) —C(=O)R$_{27}$,
   (c) pyridinyl,
   (d) 2-pyrimidinyl,
   (e) 4-pyrimidinyl, or
   (f) pyridazinyl;
wherein groups (c) to (f) may be substituted with amino, methyl, F, or Cl; wherein R$_{27}$ is as defined in claim 1.

12. A compound of formula I according to claim 11 wherein R$_{27}$ is
   (a) C$_{1-3}$ alkyl,
   (b) C$_{1-2}$ alkylhydroxyl, or
   (c)

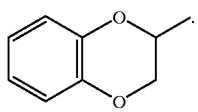

13. A compound of formula I according to claim 1 which is
   a. (±)-N-[[4,5-Dihydro-3-[4-(1H-imidazol-1-yl)phenyl]-5-isoxazolyl]methyl]acetamide,
   b. (±)-N-[[4,5-Dihydro-3-[4-[4-(hydroxyacetyl)-1-piperazinyl]phenyl]-5-isoxazolyl]methyl]acetamide,
   c. (±)-N-[[3-[3-Fluoro-4-(1-piperazinyl)phenyl]-4,5-dihydro-5-isoxazolyl]methyl]acetamide,
   d. (±)-N-[[3-[3-Fluoro-4-[4-(hydroxyacetyl)-1-piperazinyl]phenyl]-4,5-dihydro-5-isoxazolyl]methyl]acetamide,
   e. (±)-N-[[3-[3-Fluoro-4-(1-pyrrolidinyl)phenyl]-4,5-dihydro-5-isoxazolyl]methyl]acetamide,
   f. (±)-N-[[3-[3-Fluoro-4-(1H-imidazol-1-yl)phenyl]-4,5-dihydro-5-isoxazolyl]methyl]acetamide,
   g. (±)-N-[[3-[4-(4-Cyano-1H-pyrazol-1-yl)-3-fluorophenyl]-4,5-dihydro-5-isoxazolyl]methyl]acetamide,
   h. (±)-N-[[3-[4-(4-Cyano-1H-1,2,3-triazol-1-yl)-3-fluorophenyl]-4,5-dihydro-5-isoxazolyl]methyl]acetamide,
   i. (±)-N-[[3-[3,5-Difluoro-4-(1-piperazinyl)phenyl]-4,5-dihydro-5-isoxazolyl]methyl]acetamide,
   j. (±)-N-[[3-[3,5-Difluoro-4-(4-morpholinyl)phenyl]-4,5-dihydro-5-isoxazolyl]methyl]acetamide,
   k. (−)-N-[[3-[3-Fluoro-4-(1-pyrrolidinyl)phenyl]-4,5-dihydro-5-isoxazolyl]methyl]acetamide,
   l. (−)-N-[[3-[3-Fluoro-4-(1H-pyrrol-1-yl)phenyl]-4,5-dihydro-5-isoxazolyl]methyl]acetamide,
   m. (−)-N-[[3-[3-Fluoro-4-(1H-imidazol-1-yl)phenyl]-4,5-dihydro-5-isoxazolyl]methyl]acetamide,
   n. (−)-N-[[3-[4-(4-Cyano-1H-pyrazol-1-yl)-3-fluorophenyl]-4,5-dihydro-5-isoxazolyl]methyl]acetamide,
   o. (−)-N-[[3-[3-Fluoro-4-(3-formyl-1H-pyrrol-1-yl)phenyl]-4,5-dihydro-5-isoxazolyl]methyl]acetamide,
   p. (−)-N-[[3-[3-Fluoro-4-[3-[(hydroxyimino)methyl]-1H-pyrrol-1-yl]phenyl]-4,5-dihydro-5-isoxazolyl]methyl]acetamide,
   q. (−)-N-[[3-[4-(3-Cyano-1H-pyrrol-1-yl)-3-fluorophenyl]-4,5-dihydro-5-isoxazolyl]methyl]acetamide,
   r. (−)-N-[[3-[3-Fluoro-4-(1H-pyrrol-1-yl)phenyl]-4,5-dihydro-5-isoxazolyl]methyl]ethanethioamide,
   s. (+)-N-[[3-[3-Fluoro-4-(3-formyl-1H-pyrrol-1-yl)phenyl]-4,5-dihydro-5-isoxazolyl]methyl]ethanethioamide,
   t. (−)-N-[[3-[3-Fluoro-4-[3-(hydroxymethyl)-1H-pyrrol-1-yl]phenyl]-4,5-dihydro-5-isoxazolyl]methyl]acetamide,
   u. (−)-N-[[3-[4-(4-Acetyl-1-piperazinyl)-3-fluorophenyl]-4,5-dihydro-5-isoxazolyl]methyl]acetamide,
   v. (−)-N-[[3-[4-[4-[(2,3-Dihydro-1,4-benzodioxin-2-yl)carbonyl]-1-piperazinyl]-3-fluorophenyl]-4,5-dihydro-5-isoxazolyl]methyl]acetamide,
   w. (−)-N-[[3-[3-Fluoro-4-(hydroxyacetyl)-1-piperazinyl]phenyl]-4,5-dihydro-5-isoxazolyl]methyl]acetamide,
   x. (−)-N-[[3-[3-Fluoro-4-(4-morpholinyl)phenyl]-4,5-dihydro-5-isoxazolyl]methyl]acetamide,
   y. (−)-N-[[3-[3,5-Difluoro-4-(1-piperazinyl)phenyl]-4,5-dihydro-5-isoxazolyl]methyl]-acetamide,
   z. (−)-N-[[3-[4-[4-[(2,3-Dihydro-1,4-benzodioxin-2-yl)carbonyl]-1-piperazinyl]-3,5-difluorophenyl]-4,5-dihydro-5-isoxazolyl]methyl]acetamide,
   aa. (−)-N-[[3-[3,5-Difluoro-4-[4-(hydroxyacetyl)-1-piperazinyl]phenyl]-4,5-dihydro-5-isoxazolyl]methyl]acetamide,
   bb. (−)-N-[[3-[3,5-Difluoro-4-(1H-imidazol-1-yl)phenyl]-4,5-dihydro-5-isoxazolyl]methyl]acetamide,
   cc. N-[[3-[3,5-Difluoro-4-(1H-imidazol-1-yl)phenyl]-4,5-dihydro-5-isoxazolyl]methyl]ethanethioamide,
   dd. (−)-N-[[3-[3,5-Difluoro-4-(4-morpholinyl)phenyl]-4,5-dihydro-5-isoxazolyl]methyl]ethanethioamide,
   ee. (−)-N-[[3-[3,5-Difluoro-4-(4-morpholinyl)phenyl]-4,5-dihydro-5-isoxazolyl]methyl]acetamide,
   ff. N-({3-[3-fluoro-4-(4-thiomorpholinyl)phenyl]-4,5-dihydro-5-isoxazolyl}methyl)acetamide, gg. N-({3-[3-fluoro-4-(1-oxo-1lambda$^4$,4-thiazinan-4-yl)phenyl}-4,5-dihydro-5-isoxazolyl}methyl)acetamide, hh. N-({3-[3-fluoro-4-(4-thiomorpholinyl)phenyl]-4,5-dihydro-5-isoxazolyl}methyl)ethanethioamide, or ii. N-({3-[3-fluoro-4-(1-oxo-1lambda$^4$,4-thiazinan-4-yl)phenyl}-4,5-dihydro-5-isoxazolyl}methyl)ethanethioamide.

14. A method for treating microbial infections in patients comprising:

administering to a patient in need thereof an effective amount of a compound of formula I as shown in claim 1.

15. The method of claim 14 wherein said compound of formula I is administered orally, parenterally, topically or transdermally in a pharmaceutical composition.

16. The method of claim 14 wherein said compound of formula I is administered orally in a pharmaceutical composition.

17. The method of claim 14 wherein said compound is administered in an amount of from about 0.1 to about 100 mg/kg of body weight/day.

18. A pharmaceutical composition comprising a compound of claim 1 and a pharmaceutically acceptable carrier.

* * * * *